United States Patent
Abbott et al.

(10) Patent No.: US 9,797,843 B2
(45) Date of Patent: Oct. 24, 2017

(54) SUBSTRATES, DEVICES, AND METHODS FOR QUANTITATIVE LIQUID CRYSTAL ASSAYS

(71) Applicant: Platypus Technologies, LLC, Madison, WI (US)

(72) Inventors: Nicholas Abbott, Madison, WI (US); Christopher Murphy, Madison, WI (US); Barbara Israel, Mount Horeb, WI (US)

(73) Assignee: PLATYPUS TECHNOLOGIES, LLC, Madison, WI (US)

( * ) Notice: Subject to any disclaimer, the term of this patent is extended or adjusted under 35 U.S.C. 154(b) by 74 days.

(21) Appl. No.: 14/811,083

(22) Filed: Jul. 28, 2015

(65) Prior Publication Data

US 2016/0025636 A1    Jan. 28, 2016

Related U.S. Application Data

(60) Continuation of application No. 13/369,062, filed on Feb. 8, 2012, now Pat. No. 9,103,794, which is a continuation of application No. 12/694,678, filed on Jan. 27, 2010, now abandoned, which is a division of application No. 10/227,974, filed on Aug. 26, 2002, now Pat. No. 7,666,661.

(60) Provisional application No. 60/315,203, filed on Aug. 27, 2001.

(51) Int. Cl.
C12M 1/34      (2006.01)
G01N 21/75     (2006.01)
B82Y 30/00     (2011.01)

(52) U.S. Cl.
CPC .............. *G01N 21/75* (2013.01); *B82Y 30/00* (2013.01); *Y10T 436/143333* (2015.01)

(58) Field of Classification Search
None
See application file for complete search history.

(56) References Cited

U.S. PATENT DOCUMENTS

| | | |
|---|---|---|
| 2,639,815 A | 5/1953 | Paluck |
| 3,645,693 A | 2/1972 | Poziomek |
| 3,883,398 A | 5/1975 | Ono |
| 4,068,925 A | 1/1978 | Tani |
| 4,096,086 A | 6/1978 | Kanbe |
| 4,285,697 A | 8/1981 | Neary |
| 4,551,264 A | 11/1985 | Eidenschink |
| 4,597,942 A | 7/1986 | Meathrel |
| 4,612,873 A | 9/1986 | Eberle |
| 4,795,253 A | 1/1989 | Sandridge |
| 4,927,879 A | 5/1990 | Pidgeon |
| 5,055,408 A | 10/1991 | Higo |
| 5,059,394 A | 10/1991 | Phillips |
| 5,063,024 A | 11/1991 | Partanen |
| 5,073,294 A | 12/1991 | Shannon |
| 5,132,226 A | 7/1992 | Dreher |
| 5,141,718 A | 8/1992 | Clark |
| 5,298,394 A | 3/1994 | Arima |
| 5,302,515 A | 4/1994 | Goodwin |
| 5,355,215 A | 10/1994 | Schroeder |
| 5,370,841 A | 12/1994 | McDonnel |
| 5,474,796 A | 12/1995 | Brennan |
| 5,484,565 A | 1/1996 | Larsen |
| 5,599,919 A | 2/1997 | Yen |
| 5,601,980 A | 2/1997 | Gordon |
| 5,700,637 A | 12/1997 | Southern |
| 5,801,055 A | 9/1998 | Henderson |
| 5,858,659 A | 1/1999 | Sapolsky |
| 5,908,786 A | 6/1999 | Moreno |
| 5,925,525 A | 7/1999 | Fodor |
| 5,985,551 A | 11/1999 | Brennan |
| 6,001,311 A | 12/1999 | Brennan |
| 6,017,696 A | 1/2000 | Heller |
| 6,040,193 A | 3/2000 | Winkler |
| 6,045,996 A | 4/2000 | Cronin |
| 6,051,380 A | 4/2000 | Sosnowski |
| 6,068,818 A | 5/2000 | Ackley |
| 6,171,780 B1 | 1/2001 | Pham |
| 6,171,802 B1 | 1/2001 | Woolverton |
| 6,201,588 B1 | 3/2001 | Walton |
| 6,242,266 B1 | 6/2001 | Schleifer |
| 6,277,489 B1 | 8/2001 | Abbott |

(Continued)

FOREIGN PATENT DOCUMENTS

| | | |
|---|---|---|
| EP | 1549953 | 12/2006 |
| GB | 2297549 | 7/1996 |

(Continued)

OTHER PUBLICATIONS

Gupta et al., ["Optical Amplification of Ligand-Receptor Binding Using Liquid Crystals", Science, vol. 279, Mar. 27, 1998, pp. 2077-2080].*

Bernard, et al., "Affinity capture of proteins from solution and their dissociation by contact printing," Nature Biotechnology (2001) 19(9):866-869.

Drawhorn et al., "Anchoring of Nematic Liquid Crystals on Self-Assembled Monolayers Formed from Alkanethiols on Semitransparent Films of Gold," J. Phys. Chem. (1995) 45:16511.

Dulcey C.S., "Deep UV Photochemistry of Chemisorbed Monolayers: Patterned Coplanar Molecular Assemblies", Science, American Association for the Advancement of Science, 1991, vol. 252, No. 5005, pp. 551-554.

Espinoza et al. Orientational Behavior of Thermotropic Liquid Crystals on Surfaces Presenting Electrostatically Bound Vesicular Stomatitis Virus. Langmuir Mar. 16, 2004; 20(6):2375-85.

Fast, Cheap, and Portable: A New Pathogen Detection Tool. Biomedical Instrumentation & Technology.2002; 36(1):15.

Goto et al., "Design of an Aberration-Free Spherical Micro Lens with a Diffractive Relief Granting Film on a Refractive Spherical Glass Substrate," Jpn. J. AppL Phys. (1992) 31:1586.

(Continued)

*Primary Examiner* — Ann Lam
(74) *Attorney, Agent, or Firm* — Casimir Jones S.C.

(57) ABSTRACT

The present invention relates to the field of molecular diagnostics, and in particular to diagnostics based on a liquid crystal assay format. In particular, the present invention provided improved substrates and methods of using liquid crystal assays for quantitating the amount of an analyte in a sample. The present invention also provides materials and methods for detecting non-specific binding of an analyte to a substrate by using a liquid crystal assay format.

15 Claims, 7 Drawing Sheets

(56) References Cited

U.S. PATENT DOCUMENTS

| | | |
|---|---|---|
| 6,277,490 B1 | 8/2001 | Ruf |
| 6,284,197 B1 | 9/2001 | Abbott |
| 6,288,392 B1 | 9/2001 | Abbott |
| 6,306,659 B1 | 10/2001 | Parce |
| 6,410,687 B1 | 6/2002 | Vale |
| 6,444,254 B1 | 9/2002 | Chilkoti |
| 6,468,657 B1 | 10/2002 | Hou |
| 6,527,115 B2 | 3/2003 | Rabiner et al. |
| 6,586,257 B1 | 7/2003 | Vuong |
| 6,596,545 B1 | 7/2003 | Wagner |
| 6,632,655 B1 | 10/2003 | Mehta |
| 6,692,699 B2 | 2/2004 | Abbott |
| 6,780,492 B2 | 8/2004 | Abbott |
| 6,797,463 B2 | 9/2004 | Abbott |
| 6,811,752 B2 | 11/2004 | Barbera-Guillem |
| 6,824,837 B2 | 11/2004 | Abbott |
| 6,844,184 B2 | 1/2005 | Kim |
| 6,849,321 B2 | 2/2005 | Abbott |
| 6,852,285 B2 | 2/2005 | Abbott |
| 6,858,423 B1 | 2/2005 | Abbott |
| 6,884,357 B2 | 4/2005 | Siddiqi |
| 6,982,171 B2 | 1/2006 | Kim |
| 7,018,838 B2 | 3/2006 | Murphy |
| 7,125,592 B2 | 10/2006 | Abbott |
| 7,135,143 B2 | 11/2006 | Abbott |
| 7,303,694 B2 | 12/2007 | Abbott |
| 7,332,328 B2 | 2/2008 | Webb |
| 7,371,563 B2 | 5/2008 | Duffy |
| 7,374,906 B2 | 5/2008 | Kirk |
| 7,390,463 B2 | 6/2008 | He et al. |
| 7,452,726 B2 | 11/2008 | Chou |
| 7,459,124 B2 | 12/2008 | Abbott |
| 7,662,572 B2 | 2/2010 | Abbott et al. |
| 7,662,751 B2 | 2/2010 | Abbott |
| 7,666,661 B2 | 2/2010 | Abbott |
| 7,732,152 B2 | 6/2010 | Abbott |
| 7,807,348 B2 | 10/2010 | Abbott |
| 7,842,499 B2 | 11/2010 | Abbott |
| 7,910,382 B2 | 3/2011 | Abbott |
| 7,951,577 B2 | 5/2011 | Murphy |
| 8,268,614 B2 | 9/2012 | Murphy et al. |
| 2002/0004216 A1 | 1/2002 | Abbott |
| 2002/0028451 A1 | 3/2002 | Abbott |
| 2002/0040805 A1* | 4/2002 | Swager ............... B82Y 15/00 174/110 A |
| 2002/0052002 A1* | 5/2002 | Niehaus .......... G01N 33/54373 435/7.1 |
| 2002/0055093 A1 | 5/2002 | Abbott |
| 2002/0117412 A1 | 8/2002 | Rabiner |
| 2002/0123134 A1 | 9/2002 | Huang |
| 2002/0142453 A1 | 10/2002 | Abbott |
| 2002/0164604 A1 | 11/2002 | Abbott |
| 2002/0172621 A1 | 11/2002 | Barbera-Guillem |
| 2002/0173033 A1 | 11/2002 | Hammerick |
| 2002/0179439 A1* | 12/2002 | Weng ............... B01J 19/0046 506/21 |
| 2003/0032046 A1 | 2/2003 | Duffy |
| 2003/0040087 A1 | 2/2003 | Kim et al. |
| 2003/0049862 A1 | 3/2003 | He |
| 2003/0071949 A1 | 4/2003 | Abbott |
| 2003/0099993 A1 | 5/2003 | Abbott |
| 2003/0113812 A1 | 6/2003 | Hemperly |
| 2003/0124029 A1 | 7/2003 | Webb |
| 2003/0127396 A1 | 7/2003 | Siddiqi |
| 2003/0180966 A1 | 9/2003 | Abbott |
| 2003/0194753 A1 | 10/2003 | Abbott |
| 2003/0215449 A1 | 11/2003 | Mezes |
| 2004/0002131 A1 | 1/2004 | Kim |
| 2004/0009583 A1 | 1/2004 | Bennet |
| 2004/0038408 A1 | 2/2004 | Abbott |
| 2004/0091620 A1 | 5/2004 | Abbott |
| 2004/0142411 A1 | 7/2004 | Kirk |
| 2004/0161800 A1 | 8/2004 | Abbott |
| 2004/0224380 A1 | 11/2004 | Chou |
| 2005/0009113 A1 | 1/2005 | Goldbard |
| 2005/0064395 A1 | 3/2005 | Israel |
| 2005/0079486 A1 | 4/2005 | Abbott |
| 2005/0079487 A1 | 4/2005 | Abbott |
| 2005/0106562 A1 | 5/2005 | Abbott |
| 2005/0112544 A1 | 5/2005 | Xu |
| 2005/0158880 A1 | 7/2005 | Ostuni et al. |
| 2005/0221271 A1 | 10/2005 | Abbott |
| 2005/0260703 A1 | 11/2005 | Abbott |
| 2006/0003389 A1 | 1/2006 | Abbott |
| 2006/0141446 A1 | 6/2006 | Abbott |
| 2006/0252031 A1 | 11/2006 | Abbott |
| 2007/0004046 A1 | 1/2007 | Abbott |
| 2007/0042505 A1 | 2/2007 | Abbott |
| 2007/0099249 A1 | 5/2007 | Abbott |
| 2007/0104612 A1 | 5/2007 | Abbott |
| 2007/0110614 A1 | 5/2007 | Abbott |
| 2007/0231832 A1 | 10/2007 | Abbott |
| 2007/0269848 A1 | 11/2007 | Abbott |
| 2008/0050799 A1 | 2/2008 | Abbott |
| 2008/0160539 A1 | 7/2008 | Abbott |
| 2008/0187949 A1 | 8/2008 | Goldbard |
| 2009/0054262 A1 | 2/2009 | Abbott |

FOREIGN PATENT DOCUMENTS

| | | |
|---|---|---|
| WO | 91/18653 | 12/1991 |
| WO | 99/63329 | 6/1999 |
| WO | 00/50570 A2 | 8/2000 |
| WO | 00/60356 | 10/2000 |
| WO | 00/73799 | 12/2000 |
| WO | 01/61325 A2 | 8/2001 |
| WO | 01/61325 A3 | 8/2001 |
| WO | 01/61357 A2 | 8/2001 |
| WO | 01/61357 A3 | 8/2001 |
| WO | 02/071929 A2 | 9/2002 |
| WO | 02/075294 | 9/2002 |
| WO | 03/019191 | 3/2003 |
| WO | 03/021339 | 3/2003 |
| WO | 03/029481 | 4/2003 |
| WO | 03/081230 | 10/2003 |
| WO | 03/086197 | 10/2003 |
| WO | 2004/041061 | 5/2004 |
| WO | 2004/044583 | 5/2004 |
| WO | 2005/010160 | 2/2005 |
| WO | 2005/047863 | 5/2005 |
| WO | 2008/069752 | 6/2008 |

OTHER PUBLICATIONS

Green et al., "Mechanism of the Transformation of a Stiff Polymer Lyotropic Nematic Liquid Crystal to the Cholesteric State by Dopant-Mediated ChiralInformation Transfer", J. Am. Chem. Soc., 1998. 120,9810-9817.

Gupta et al., "Design of Surfaces for Patterned Alignment of Liquid Crystals on Planar and Curved Substrates," Science (1997) 276:1533-1536.

Gupta et al, "Optical Amplification of Ligand-Receptor Binding Using Liquid Crystals," Science vol. 279, Mar. 27, 1998 pp. 2077-2080.

Gupta, Vinay K., et al., "Using Droplets of Nematic Liquid Crystal to Probe the Microscopic and Mesoscopic Structure of Organic Surfaces," Langmuir 1999, 15(21)7213-7223.

Hickman et al., "Rational pattern design for in vitro cellular networks using surface photochemistry," J. Vac. Sci. Technol. 1994, 12:607 16.

Iwuoha E I et al: Reactivities of Organic Phase Biosensors 3: Electrochemical Study of Cytochrome P450 CAM Immobilized in a Methyltriethoysilance Sol-Gel Electroanalysis, VHC Publishers Inc. vol. 12, p. 980 2000.

Jerome, "Surface effects and anchoring in liquid crystals," Rep. Prog. Phys. 1991, 54:391 451.

Skaife, J. et al.. "Quantitative Interpretation of the Optical Textures of Liquid Crystals Caused by Specific Binding of Immunoglobulins to Surface-Bound Antugens," Langmuir 16(7):3529-3536 (2000).

Kikuchi H E et al, "Culture of Bone-Marrow-Derived Cells in Microfabricated Pit Arrays" Proc SPIE Int Soc Opt Eng; 2001, vol. 4265, pp. 40-49.

(56) References Cited

OTHER PUBLICATIONS

Kleinfield et al., "Controlled Outgrowth of Dissociated Neurons on Patterned Substrates," J. Neurosci. 1998, 8:4098 120.

Kumar et al., "Patterned Self-Assembled Monolayers and Meso-Scale Phenomena," Acc. Chem. Res.(1995) 28: 219.

Kumar et al., "Patterned Self-Assembled Monolayers and Meso-Scale Phenomena," Langmuir 1994, 10:1498 511.

Lauer L. et al, "Spot Complaint Neuronal Networks by Structure Optimized Micro-Contact Printing" Biomaterials, Elsevier Science, 2001, vol. 22, pp. 1925-1932.

Ladam, Guy, et al., "Protein Adsorption onto Auto-Assembled Polyelectrolyte Films," Langmuir (2001) 17(3):878-882.

Magiera et al., "Hybrid Imaging Element—Possibilities of Aberration Correction," Soc. Photo Opt. Instrum. Eng., (1996) 2774:204.

Renault et al. Fabricating Microarrays of Functional Proteins Using Affinity Contact Printing. Angew. Chem. Int. Ed. 2002; 41 (13)2320-2321.

Resler at al., "High-efficiency liquid-crystal optical phased-array beam steering," Opt. Lett.(1996) 21:689.

Kim et al., Anal. Chem. "A Possible Substrate for Biomolecular Assays Based on Lquid Crystals, Analytical 2 Chemistry," 72(19);4646-4653 (2000).

Shah, R.R., et al., "Principles for Measurement of Chemical Exposure Based on Recognition-Driven Anchoring Transitions in Liquid Crystals," Science2001, 393(5533):1296-1299.

Skaife, Justin G. et al, "Quanitative Characterization of Obliquely Deposited Subtrates of Gold by Atomic Force Microscopy: Influence of Subtrate Topography on Anchoring of Liquid Crystals" Chemistry of Materials, V 11(3) 1999, pp. 612-623.

Skaife, Justin G., et al., "Quantitative Interpretation of the Optical Textures of Liquid Crystals Caused by Specific Binding of Immunoglobulins to Surface-Bound Antugens," Langmuir 2000, 16(7):3529-3536.

Souady et al., "Structural Profiling of Individual Glycosphingolipids ina Single Thin-Layer Chromatogram by Multiple Sequential Immunodetection Matched with Direct IR-MALDI-o-TOF Mass Spectrometry," Anal. Chem. 2009, 31:9481-9492.

Stern, M.B., "Binary Optics: A VLSI-based microoptics technology," Microelectron. Eng. (1996) 32:369.

Tarlov et al., "UV Photopatteming of Alkanethiolate Monolayers," J. Am. Chem. Soc. (1993) 115: 5305.

Tingey et al. imaging of Affinity Microcontact Printed Proteins by Using Liquid Crystals. Langmuir.2004; 20:6816-6826.

Wagner et al., "Covalent Immobilization of Native Biomoleculres onto Au(111) via N-Hydroxysuccinimide Ester Functionalized Self-Assembled Monolayers for Scanning Probe Microscopy," Biophys. J.(1996) 70:2052 2066.

Wolverton, et al. A liquid crystal biosensor for virus detection. Abstracts of the General Meeting of the American Society for Microbiology. 2002;102:110-111. Abstract Only.

Xia, Y., "Use of Controlled Reactive Spreading of Liquid Alkanethiol OD the Surface of Gold to Modify the Size of Features Produced by Mierocontact Printing," Whitesides, G., J. Am. Chem. Soc. 1995, 117:327475.

Kim, et al. "Orientation of Liquid Crystals on Mechanically Rubbed Films of Bovine Serum Albumin: A possible Substrate for Biomolecular Assays Based on Liquid Crystals", Anal. Chem. vol. 72, No. 19, Oct. 1, 2000, pp. 4646-4653.

Kleinfeld et al, "Controlled Outgrowth of Dissociated Neurons on Patterned Substrates," Journal of Neuroscience, (1988) 8 (11): 4098-4120.

Charych, Deborah H., et al., "Direct Colorimetric Detection of a Receptor-Ligand Interaction by a Polymerized Bilayer Assembly," Science; 1993; 261(5121): 585-588.

Detrait et al., (Orientation of cell adhesion and growth on patterned heterogeneous polystyrene surface, 1998, Journal of Neuroscience Methods, vol. 84, pp. 193-204).

\* cited by examiner

SUBSTRATES, DEVICES, AND METHODS FOR QUANTITATIVE LIQUID CRYSTAL ASSAYS

CROSS REFERENCE TO RELATED APPLICATIONS

This application is a continuation of U.S. patent application Ser. No. 13/369,062, filed Feb. 8, 2012, which is a continuation of abandoned U.S. patent application Ser. No. 12/694,678, filed Jan. 27, 2010, which is a divisional of U.S. patent application Ser. No. 10/227,974, filed Aug. 26, 2002, allowed as U.S. Pat. No. 7,666,661, issued Feb. 23, 2010, which claims priority to U.S. Provisional Patent Application Ser. No. 60/315,203, filed Aug. 27, 2001, all of which are herein incorporated by reference in their entirety.

FIELD OF THE INVENTION

The present invention relates to the field of molecular diagnostics, and in particular to diagnostics based on a liquid crystal assay format.

BACKGROUND OF THE INVENTION

The detection of pathogen, protein, and nucleic acid targets in biological samples forms the basis of the multibillion dollar in vitro diagnostic industry. Detection of protein and nucleic acid targets can be divided into diagnostic and research based markets. The diagnostic market includes the detection and identification of pathogens such as viruses and bacteria, the identification of various genetic markers, and the identification of markers associated with the presence of tumors. The research market includes the genomics and proteomics industries, which require analytical, drug discovery, and high-throughput screening technologies.

The ability to diagnose patients at the "point of care" is expected to yield major savings to the health care industry and improve the effectiveness of treatment. For example, "point of care" testing is a requirement for the effective use of anti-influenza drugs such as RELENZA and TAMIFLU. This means that the diagnoses of influenza virus infection must be made while the patient is in the doctor's office. Recent studies in the United States indicate that that when ZSTATFLU, a rapid, influenza virus diagnostic assay was used at the point of care, healthcare costs were significantly reduced by elimination of inappropriate treatment and the timely initiation of effective therapy. As another example, the advent of personalized medicine will require genetic screening of individuals at the point of care to determine whether the individual is a candidate for particular treatment strategies or will have an adverse reaction to the preferred medication.

Currently used diagnostic assays include radioimmunoassay (RIA), enzyme-linked immunosorbent assay (ELISA), agglutination assays, surface plasmon resonance (SPR), and polymerized multilayer assemblies for the detection of receptor-ligand interactions (Charych et al., *Science* 261:585 (1993); Pan et al., *Langmuir* 13:1365 (1997)). However, most of these method requires expensive reagents (e.g., radioactively labeled antibodies or antigens), are not adaptable to microarray format (e.g., agglutinations assays), or require expensive, laboratory based equipment (e.g., SPR).

Although many of the conventional assay methods described above work very well to detect the presence of target species, they are expensive and often require instrumentation and highly trained individuals, which makes them difficult to use routinely in the field. Thus, a need exists for assay devices and systems which are easier to use and which allow for evaluation of samples in remote locations.

SUMMARY OF THE INVENTION

The present invention relates to the field of molecular diagnostics, and in particular to diagnostics based on a liquid crystal assay format. Accordingly, in some embodiments, the present invention provides methods comprising providing a sample suspected of containing an analyte and a liquid crystal assay device; adding the analyte to the liquid crystal assay device under conditions such that the presence of the analyte causes a detectable ordering of mesogens in the liquid crystal assay device; and quantitating the amount of the analyte in the sample based on the detectable ordering of mesogens. The present invention is not limited to any particular liquid crystal assay device. Indeed, the use of a variety of liquid crystal assay devices is contemplated, including, but not limited to, crystal assay device comprising a first substrate having a surface, the surface comprising a recognition moiety; and a mesogenic layer oriented on the surface. In some preferred embodiments, the liquid crystal assay device further comprises an interface between the mesogenic layer and a member selected from the group consisting of gases, liquids, solids, and combinations thereof. In other preferred embodiments, the recognition moiety is attached to the surface by an interaction which is a member selected from the group consisting of covalent bonding, ionic bonding, chemisorption, physisorption, and combinations thereof. In still other embodiments, the surface further comprises an organic layer. In further preferred embodiments, the recognition moiety is attached to the organic layer by an interaction which is a member selected from the group consisting of covalent bonding, ionic bonding, chemisorption, physisorption, and combinations thereof. The present invention is not limited to any particular recognition moiety. Indeed, the use of a variety of recognition moieties is contemplated, including, but not limited to those selected from the group consisting of polynucleotides, antigen binding molecules, and polypeptides. Likewise, the methods of the present invention are not limited to the detection of any particular analyte. Indeed, the detection of a variety of analytes is contemplated, including, but not limited to those selected from the group consisting of polypeptides, polynucleotides, organic analytes, and pathogens.

In additional preferred embodiments, the mesogenic layer comprises a polymeric mesogen. The present invention is not limited to the use of a particular mesogen. Indeed, the use of a variety of mesogens is contemplated, including, but not limited to mesogens selected from the group consisting of 4-cyano-4'-pentylbiphenyl, N-(4-methoxybenzylidene)-4-butlyaniline and combinations thereof. In other embodiments, the mesogenic layer comprises a lyotropic liquid crystal. The present invention is not limited to any particular surface. Indeed, the present invention contemplates the use of a variety of surfaces, including, but not limited to, metal surfaces and polymeric surfaces. In some particularly preferred embodiments, the surface is a metal surface. The present invention is not limited to any particular metal surface. Indeed, the use of a variety of metal surfaces is contemplated, including, but not limited to, metal surfaces selected from the group consisting of gold, platinum, palladium, copper, nickel, silver, and combinations thereof. The present invention is not limited to any particular substrate.

Indeed, the use of a variety of substrates is contemplated, including, but not limited to substrates selected from the group consisting of flexible substrates, rigid substrates, optically opaque substrates, optically transparent substrates, conducting substrates, semiconducting substrates, and combinations thereof. In still further embodiments, the substrate is selected from the group consisting of inorganic crystals, inorganic glasses, inorganic oxides, metals, organic polymers, and combinations thereof. The present invention is not limited to any particular organic polymer. Indeed, the use of a variety of organic polymers is contemplated including, but not limited to, organic polymers selected from the group consisting of polyvinylidene fluoride, polydimethylsiloxane, polycarbonate, polystyrene, polyurethane, polyisocyanoacrylate, epoxy and combinations thereof.

In some further preferred embodiments, the substrate is heterogenous. The present invention is not limited to any particular type of heterogeneity. Indeed, the present invention contemplates that a variety of heterogenous substrates may be utilized. In some preferred embodiments, the heterogeneity is a gradient of topography across the surface. In some particularly preferred embodiments, a difference in liquid crystal orientation across the gradient of topography is correlated to the concentration of the analyte in the sample.

In other embodiments, the device further comprises a dichroic or fluorescent dye in the mesogenic layer. In still further embodiments, the method further comprises the step of measuring the amount of light transmitted by the device, wherein the amount of light transmitted is proportional to the amount of the analyte in the sample.

In still other embodiments, the quantitating step comprises illuminating the liquid crystal assay device with a specific wavelength of light to determine the degree of disorder introduced into the liquid crystal assay device. In still further embodiments, the methods further comprise the step of measuring the amount of light transmitted by the device, wherein the amount of light transmitted is proportional to the amount of the analyte in the sample. In some embodiments, the quantitating step is performed with a plate reader. In further embodiments, the plate reader is utilized to detect the detectable ordering of mesogens, wherein the detectable ordering of mesogens is accompanied by a change selected from the group consisting of a change in fluorescence, transmittance, birefringence, and absorbance changes that accompany the reorientation of the liquid crystal.

In some preferred embodiments, the quantitating step is performed by measurement of the threshold electrical field required to change the ordering of the mesogens. Accordingly, in other preferred embodiments, the liquid crystal assay device further comprises electrodes, wherein the electrodes apply an electric field across the device.

In still other embodiments, the present invention provides systems for detecting an analyte in a sample comprising at least one substrate having a surface comprising recognition moieties; a mesogenic layer oriented on the surface; and electrodes configured to apply an electrical field across the surface. In other embodiments, the system further comprises an interface between the mesogenic layer and a member selected from the group consisting of gases, liquids, solids, and combinations thereof. In further embodiments, the recognition moiety is attached to the surface by an interaction which is a member selected from the group consisting of covalent bonding, ionic bonding, chemisorption, physisorption, and combinations thereof. As described in more detail above, the present invention is not limited to any particular organic layer, substrate, surface, recognition moiety, analyte, mesogen, or organic polymer.

In other embodiments, the present invention provides systems for detecting an analyte in a sample comprising at least one substrate having a surface comprising recognition moieties; and a mesogenic layer oriented on the surface, wherein the mesogenic layer comprises a compound selected from the group consisting of a dichroic dye and a fluorescent compound. The present invention is not limited to any particular dichroic dye or fluorescent compound. Indeed, the use of a variety of dichroic dyes and fluorescent compounds is contemplated, including, but not limited to those selected from the group consisting of azobenzene, BTBP, polyazocompunds, anthraquinone, perylene dyes, and combination thereof. In some preferred embodiments, the fluorescent compound is BTBP. In other embodiments, the system further comprises an interface between the mesogenic layer and a member selected from the group consisting of gases, liquids, solids, and combinations thereof. In further embodiments, the recognition moiety is attached to the surface by an interaction which is a member selected from the group consisting of covalent bonding, ionic bonding, chemisorption, physisorption, and combinations thereof. As described in more detail above, the present invention is not limited to any particular organic layer, substrate, surface, recognition moiety, analyte, mesogen, or organic polymer.

In still further embodiments, the present invention provides systems for detecting an analyte in a sample comprising at least one substrate having a surface comprising recognition moieties, wherein the surface is heterogenous; and a mesogenic layer oriented on the surface. The present invention is not limited to any particular type of heterogeneity. Indeed, the present invention contemplates that a variety of heterogenous substrates may be utilized. In some preferred embodiments, the heterogeneity is a gradient of topography across the surface. In some particularly preferred embodiments, a difference in liquid crystal orientation across the gradient of topography is correlated to the concentration of the analyte in the sample. In other embodiments, the system further comprises an interface between the mesogenic layer and a member selected from the group consisting of gases, liquids, solids, and combinations thereof. In further embodiments, the recognition moiety is attached to the surface by an interaction which is a member selected from the group consisting of covalent bonding, ionic bonding, chemisorption, physisorption, and combinations thereof. As described in more detail above, the present invention is not limited to any particular organic layer, substrate, surface, recognition moiety, analyte, mesogen, or organic polymer.

In still other embodiments, the present invention provides methods comprising providing a substrate having at least one surface and at least one analyte; nonspecifically binding at least one analyte to the substrate; contacting the at least one surface with a mesogenic layer; and detecting binding of the at least one analyte to substrate, wherein the binding causes a reorientation of the mesogenic layer that can be detected. In some embodiments, the surface further comprises an organic layer. As described in more detail above, the present invention is not limited to any particular organic layer, substrate, surface, recognition moiety, analyte, mesogen, or organic polymer.

In further embodiments, the present invention provides methods comprising providing a substrate having at least one surface; and nanoblasting the substrate under conditions such that the surface uniformly orients mesogens when the substrate is contacted with a mesogenic layer. In some embodiments, the method further comprise the step of attaching a recognition moiety to the substrate. In still other embodiments, the methods further comprise the step of attaching an organic layer to the substrate. In other embodiments, the system further comprises an interface between the mesogenic layer and a member selected from the group consisting of gases, liquids, solids, and combinations thereof. In further embodiments, the recognition moiety is attached to the surface by an interaction which is a member selected from the group consisting of covalent bonding, ionic bonding, chemisorption, physisorption, and combinations thereof. As described in more detail above, the present invention is not limited to any particular organic layer, substrate, surface, recognition moiety, analyte, mesogen, or organic polymer.

In still other embodiments, the present invention provides methods comprising providing a substrate having at least one surface; and stretching the substrate under conditions such that the surface uniformly orients mesogens when the substrate is contacted with a mesogenic layer. In some embodiments, the method further comprises the step of attaching a recognition moiety to the substrate. In still other embodiments, the methods further comprise the step of attaching an organic layer to the substrate. In other embodiments, the system further comprises an interface between the mesogenic layer and a member selected from the group consisting of gases, liquids, solids, and combinations thereof. In further embodiments, the recognition moiety is attached to the surface by an interaction which is a member selected from the group consisting of covalent bonding, ionic bonding, chemisorption, physisorption, and combinations thereof. As described in more detail above, the present invention is not limited to any particular organic layer, substrate, surface, recognition moiety, analyte, mesogen, or organic polymer.

DESCRIPTION OF THE FIGURES

FIG. 7A shows uniform, aligned liquid crystal orientation. Optical textures of 5CB (cross polarizers) sandwiched between a rough glass microscope slide and a clean glass microscope slide. The optical appearance shown in FIG. 7B was obtained after rotation of cell A by 45°.

DEFINITIONS

Figure 1:
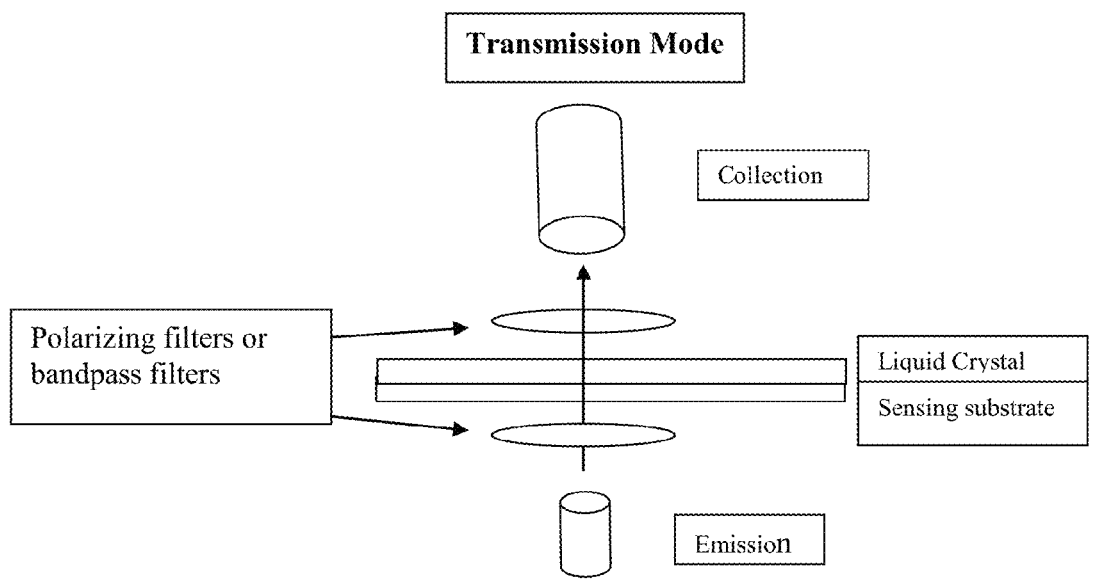
FIG. 1 is schematic depiction of a plate reading device of the present invention.

As used herein, the term "immobilization" refers to the attachment or entrapment, either chemically or otherwise, of a material to another entity (e.g., a solid support) in a manner that restricts the movement of the material.

As used herein, the terms "material" and "materials" refer to, in their broadest sense, any composition of matter.

As used herein the term "polypeptide" is used in its broadest sense to refer to all molecules or molecular assemblies containing two or more amino acids. Such molecules include, but are not limited to, proteins, peptides, enzymes, antibodies, receptors, lipoproteins, and glycoproteins.

As used herein the term "antigen binding protein" refers to a glycoprotein evoked in an animal by an immunogen (antigen) and to proteins derived from such glycoprotein (e.g., single chain antibodies and F(ab')2, Fab' and Fab fragments). An antibody demonstrates specificity to the immunogen, or, more specifically, to one or more epitopes contained in the immunogen. Native antibody comprises at least two light polypeptide chains and at least two heavy polypeptide chains. Each of the heavy and light polypeptide chains contains at the amino terminal portion of the polypeptide chain a variable region (i.e., VH and VL respectively), which contains a binding domain that interacts with antigen. Each of the heavy and light polypeptide chains also comprises a constant region of the polypeptide chains (generally the carboxy terminal portion) which may mediate the binding of the immunoglobulin to host tissues or factors influencing various cells of the immune system, some phagocytic cells and the first component (Clq) of the classical complement system. The constant region of the light chains is referred to as the "CL region," and the constant region of the heavy chain is referred to as the "CH region." The constant region of the heavy chain comprises a CH1 region, a CH2 region, and a CH3 region. A portion of the heavy chain between the CH1 and CH2 regions is referred to as the hinge region (i.e., the "H region"). The constant region of the heavy chain of the cell surface form of an antibody further comprises a spacer-transmembranal region (M1) and a cytoplasmic region (M2) of the membrane carboxy terminus. The secreted form of an antibody generally lacks the M1 and M2 regions.

As used herein, the term "analytes" refers to any material that is to be analyzed. Such materials can include, but are not limited to, ions, molecules, proteins, nucleic acids, antigens, bacteria, compounds, viruses, cells, antibodies, and cell parts.

As used herein, the term "selective binding" refers to the binding of one material to another in a manner dependent upon the presence of a particular molecular structure (i.e., specific binding). For example, a receptor will selectively bind ligands that contain the chemical structures complementary to the ligand binding site(s). This is in contrast to "non-selective binding," whereby interactions are arbitrary and not based on structural compatibilities of the molecules.

As used herein, the term "conformational change" refers to the alteration of the molecular structure of a substance. It is intended that the term encompass the alteration of the structure of a single molecule or molecular aggregate (e.g., the change in structure of a receptor upon binding a ligand).

As used herein, the term "pathogen" refers to disease causing organisms, microorganisms, or agents including, but not limited to, viruses, bacteria, parasites (including, but not limited to, organisms within the phyla Protozoa, Platyhelminthes, Aschelminthes, Acanthocephala, and Arthropoda), fungi, and prions.

As used herein, the term "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces*, and *Rickettsia*. All forms of bacteria are included within this definition including cocci, bacilli, spirochetes, spheroplasts, protoplasts, etc. "Gram negative" and "gram positive" refer to staining patterns obtained with the Gram-staining process which is well known in the art (See e.g., Finegold and Martin, Diagnostic Microbiology, 6th Ed. (1982), C V Mosby St. Louis, pp 13-15).

As used herein, the term "polymerization" encompasses any process that results in the conversion of small molecular monomers into larger molecules consisting of repeated units. Typically, polymerization involves chemical cross-linking of monomers to one another.

As used herein, the term "membrane receptors" refers to constituents of membranes that are capable of interacting with other molecules or materials. Such constituents can include, but are not limited to, proteins, lipids, carbohydrates, and combinations thereof.

As used herein, the term "volatile organic compound" or "VOC" refers to organic compounds that are reactive (i.e., evaporate quickly, explosive, corrosive, etc.), and typically are hazardous to human health or the environment above certain concentrations. Examples of VOCs include, but are not limited to, alcohols, benzenes, toluenes, chloroforms, and cyclohexanes.

As used herein, the term "enzyme" refers to molecules or molecule aggregates that are responsible for catalyzing chemical and biological reactions. Such molecules are typically proteins, but can also comprise short peptides, RNAs, ribozymes, antibodies, and other molecules.

As used herein, the term "drug" refers to a substance or substances that are used to diagnose, treat, or prevent diseases or conditions. Drugs act by altering the physiology of a living organism, tissue, cell, or in vitro system that they are exposed to. It is intended that the term encompass antimicrobials, including, but not limited to, antibacterial, antifungal, and antiviral compounds. It is also intended that the term encompass antibiotics, including naturally occurring, synthetic, and compounds produced by recombinant DNA technology.

As used herein, the term "carbohydrate" refers to a class of molecules including, but not limited to, sugars, starches, cellulose, chitin, glycogen, and similar structures. Carbohydrates can also exist as components of glycolipids and glycoproteins.

As used herein, the term "antigen" refers to any molecule or molecular group that is recognized by at least one antibody. By definition, an antigen must contain at least one epitope (i.e., the specific biochemical unit capable of being recognized by the antibody). The term "immunogen" refers to any molecule, compound, or aggregate that induces the production of antibodies. By definition, an immunogen must contain at least one epitope (i.e., the specific biochemical unit capable of causing an immune response).

As used herein, the term "chelating compound" refers to any compound composed of or containing coordinate links that complete a closed ring structure. The compounds can combine with metal ions, attached by coordinate bonds to at least two of the nonmetal ions.

As used herein, the term "recognition moiety" refers to any molecule, molecular group, or molecular complex that is capable of recognizing (i.e., specifically interacting with) a molecule. For example, the ligand binding site of a receptor would be considered a molecular recognition complex.

As used herein, the terms "home testing" and "point of care testing" refer to testing that occurs outside of a laboratory environment. Such testing can occur indoors or outdoors at, for example, a private residence, a place of business, public or private land, in a vehicle, as well as at the patient's bedside.

As used herein, the term "virus" refers to minute infectious agents, which with certain exceptions, are not observable by light microscopy, lack independent metabolism, and are able to replicate only within a living host cell. The individual particles (i.e., virions) consist of nucleic acid and a protein shell or coat; some virions also have a lipid containing membrane. The term "virus" encompasses all types of viruses, including animal, plant, phage, and other viruses.

As used herein, term "nanostructures" refers to microscopic structures, typically measured on a nanometer scale. Such structures include various three-dimensional assemblies, including, but not limited to, liposomes, films, multilayers, braided, lamellar, helical, tubular, and fiber-like shapes, and combinations thereof. Such structures can, in some embodiments, exist as solvated polymers in aggregate forms such as rods and coils. Such structures can also be formed from inorganic materials, such as prepared by the physical deposition of a gold film onto the surface of a solid, proteins immobilized on surfaces that have been mechanically rubbed, and polymeric materials that have been molded or imprinted with topography by using a silicon template prepared by electron beam lithography.

As used the term "multilayer" refers to structures comprised of two or more monolayers. The individual monolayers may chemically interact with one another (e.g., through covalent bonding, ionic interactions, van der Waals' interactions, hydrogen bonding, hydrophobic or hydrophilic assembly, and stearic hindrance) to produce a film with novel properties (i.e., properties that are different from those of the monolayers alone).

As used herein, the terms "self-assembling monomers" and "lipid monomers" refer to molecules that spontaneously associate to form molecular assemblies. In one sense, this can refer to surfactant molecules that associate to form surfactant molecular assemblies. The term "self-assembling monomers" includes single molecules (e.g., a single lipid molecule) and small molecular assemblies (e.g., polymerized lipids), whereby the individual small molecular assemblies can be further aggregated (e.g., assembled and polymerized) into larger molecular assemblies.

As used herein, the term "ligands" refers to any ion, molecule, molecular group, or other substance that binds to another entity to form a larger complex. Examples of ligands include, but are not limited to, peptides, carbohydrates, nucleic acids, antibodies, or any molecules that bind to receptors.

As used herein, the terms "organic matrix" and "biological matrix" refer to collections of organic molecules that are assembled into a larger multi-molecular structure. Such structures can include, but are not limited to, films, monolayers, and bilayers. As used herein, the term "organic monolayer" refers to a thin film comprised of a single layer of carbon-based molecules. In one embodiment, such monolayers can be comprised of polar molecules whereby the hydrophobic ends all line up at one side of the monolayer. The term "monolayer assemblies" refers to structures comprised of monolayers. The term "organic polymetric matrix" refers to organic matrices whereby some or all of the molecular constituents of the matrix are polymerized.

As used herein, the term "linker" or "spacer molecule" refers to material that links one entity to another. In one sense, a molecule or molecular group can be a linker that is covalent attached two or more other molecules (e.g., linking a ligand to a self-assembling monomer).

As used herein, the term "bond" refers to the linkage between atoms in molecules and between ions and molecules in crystals. The term "single bond" refers to a bond with two electrons occupying the bonding orbital. Single bonds between atoms in molecular notations are represented by a single line drawn between two atoms (e.g., C—C). The term "double bond" refers to a bond that shares two electron pairs. Double bonds are stronger than single bonds and are more reactive. The term "triple bond" refers to the sharing of three electron pairs. As used herein, the term "ene-yne" refers to alternating double and triple bonds. As used herein the terms "amine bond," "thiol bond," and "aldehyde bond" refer to any bond formed between an amine group (i.e., a chemical group derived from ammonia by replacement of one or more of its hydrogen atoms by hydrocarbon groups), a thiol group (i.e., sulfur analogs of alcohols), and an aldehyde group (i.e., the chemical group —CHO joined directly onto another carbon atom), respectively, and another atom or molecule.

As used herein, the term "covalent bond" refers to the linkage of two atoms by the sharing of two electrons, one contributed by each of the atoms.

As used herein, the term "spectrum" refers to the distribution of light energies arranged in order of wavelength.

As used the term "visible spectrum" refers to light radiation that contains wavelengths from approximately 360 nm to approximately 800 nm.

As used herein, the term "ultraviolet irradiation" refers to exposure to radiation with wavelengths less than that of visible light (i.e., less than approximately 360 nm) but greater than that of X-rays (i.e., greater than approximately 0.1 nm). Ultraviolet radiation possesses greater energy than visible light and is therefore, more effective at inducing photochemical reactions.

As used herein, the term "substrate" refers to a solid object or surface upon which another material is layered or attached. Solid supports include, but are not limited to, glass, metals, gels, and filter paper, among others.

As used herein, the terms "array" and "patterned array" refer to an arrangement of elements (i.e., entities) into a material or device. For example, combining several types of ligand binding molecules (e.g., antibodies or nucleic acids) into an analyte-detecting device, would constitute an array.

As used herein, the term "badge" refers to any device that is portable and can be carried or worn by an individual working in an analyte detecting environment.

As used herein, the term "biological organisms" refers to any carbon-based life forms.

As used herein, the term "in situ" refers to processes, events, objects, or information that are present or take place within the context of their natural environment.

As used herein, the term "sample" is used in its broadest sense. In one sense it can refer to a biopolymeric material. In another sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. These examples are not to be construed as limiting the sample types applicable to the present invention.

As used herein, the term "liquid crystal" refers to a thermodynamic stable phase characterized by anisotropy of properties without the existence of a three-dimensional crystal lattice, generally lying in the temperature range between the solid and isotropic liquid phase.

As used herein, the term "mesogen" refers compounds that form liquid crystals, and in particular rigid rodlike or disclike molecules which are components of liquid crystalline materials.

As used herein, "thermotropic liquid crystal" refers to liquid crystals which result from the melting of mesogenic solids due to an increase in temperature. Both pure substances and mixtures form thermotropic liquid crystals.

"Lyotropic," as used herein, refers to molecules which form phases with orientational and/or positional order in a solvent. Lyotropic liquid crystals can be formed using amphiphilic molecules (e.g., sodium laurate, phosphatidylethanolamine, lecithin). The solvent can be water.

As used herein, the term "heterogenous surface" refers to a surface that orients liquid crystals in at least two separate planes or directions, such as across a gradient.

As used herein, "nematic" refers to liquid crystals in which the long axes of the molecules remain substantially parallel, but the positions of the centers of mass are randomly distributed. Nematic liquid crystals can be substantially oriented by a nearby surface.

"Chiral nematic," as used herein refers to liquid crystals in which the mesogens are optically active. Instead of the director being held locally constant as is the case for nematics, the director rotates in a helical fashion throughout the sample. Chiral nematic crystals show a strong optical activity which is much higher than can be explained on the bases of the rotatory power of the individual mesogens. When light equal in wavelength to the pitch of the director impinges on the liquid crystal, the director acts like a diffraction grating, reflecting most and sometimes all of the light incident on it. If white light is incident on such a material, only one color of light is reflected and it is circularly polarized. This phenomenon is known as selective reflection and is responsible for the iridescent colors produced by chiral nematic crystals.

"Smectic," as used herein refers to liquid crystals which are distinguished from "nematics" by the presence of a greater degree of positional order in addition to orientational order; the molecules spend more time in planes and layers than they do between these planes and layers. "Polar smectic" layers occur when the mesogens have permanent dipole moments. In the smectic A2 phase, for example, successive layers show anti ferroelectric order, with the direction of the permanent dipole alternating from layer to layer. If the molecule contains a permanent dipole moment transverse to the long molecular axis, then the chiral smectic phase is ferroelectric. A device utilizing this phase can be intrinsically bistable.

"Frustrated phases," as used herein, refers to another class of phases formed by chiral molecules. These phases are not chiral, however, twist is introduced into the phase by an array of grain boundaries. A cubic lattice of defects (where the director is not defined) exist in a complicated, orientationally ordered twisted structure. The distance between these defects is hundreds of nanometers, so these phases reflect light just as crystals reflect x-rays.

"Discotic phases" are formed from molecules which are disc shaped rather than elongated. Usually these molecules have aromatic cores and six lateral substituents. If the molecules are chiral or a chiral dopant is added to a discotic liquid crystal, a chiral nematic discotic phase can form.

DESCRIPTION OF THE INVENTION

The present invention relates to the field of molecular diagnostics, and in particular to diagnostics based on a liquid crystal assay format. Liquid crystal-based assay systems (LC assays) are described in WO 99/63329, which is herein incorporated by reference, and Gupta et al., Science 279: 2077-2080 (1998). Seung-Ryeol Kim, Rahul R. Shah, and Nicholas L. Abbott; Orientations of Liquid Crystals on Mechanically Rubbed Films of Bovine Serum Albumin: A Possible Substrate for Biomolecular Assays Based on Liquid Crystals, Analytical Chemistry; 2000; 72(19); 4646-4653; Justin J. Skaife and Nicholas L. Abbott; Quantitative Interpretation of the Optical Textures of Liquid Crystals Caused by Specific Binding of Immunoglobulins to Surface-Bound Antigens, Langmuir; 2000; 16(7); 3529-3536; Vinay K. Gupta and Nicholas L. Abbott; Using Droplets of Nematic Liquid Crystal To Probe the Microscopic and Mesoscopic Structure of Organic Surfaces, Langmuir; 1999; 15(21); 7213-7223.

The LC assays of the present inventions are useful for detecting and quantitating a wide variety of analytes, including, but not limited to, polypeptides, polynucleotides, viruses, microorganisms (bacteria, viruses, prions, fungi and mycoplasmas), and low molecular weight compounds. It can also be used too discern subtle changes in an analyte such as the activation state of a protein associated with phosphorylation. LC assays are used to directly detect specific molecules and, in preferred embodiments, do not require labels, fluorescent dyes, colored substrates, or secondary antibodies. Furthermore, the LC assays of the present invention are readily adaptable to multi-array formats that permit simultaneous detection of more than one target molecule, virus or micro-organism and appropriate controls. Adaptability to multi-array formats also makes the LC assays of the present invention useful in high-throughput screening applications such as drug discovery. The LC assays of the present invention are also fast because the liquid crystals reorient in response to alterations in a surface in seconds. Additionally, because the LC assays of the present invention do not, in preferred embodiments, need expensive equipment to perform and interpret assay results, the LC assays are uniquely suited to on-site use and use in low-technology environments.

In some embodiments of the present invention, but not all, the LC assays comprise a substrate to which recognition moieties are attached, preferably via an organic layer on the substrate. In preferred embodiments, the substrate or organic layer serves to uniformly orient the liquid crystal. In some preferred embodiments, the substrate surface is prepared by rubbing, nanoblasting (i.e., abrasion of a surface with submicron particles to create roughness), or oblique deposition of a metal. In some embodiments, the substrate so produced provides a uniform, homogenous surface, while in other embodiments, the surface is heterogenous. In some particularly preferred embodiments, the substrate is patterned to allow quantification. When a target analyte binds to the recognition moiety, the orientation of the liquid crystal is disrupted at the discrete area of binding. According to the present invention, the disruption of orientation can be detected by a variety of methods, including viewing with crossed polars, measuring the threshold electrical field required to change the orientation of the liquid crystal, and viewing in the presence of dichroic agents. The liquid crystals can be viewed using white light or using a specific wavelength or combination of wavelengths of light.

Accordingly, the present invention provides improved substrates and devices for LC assays, including quantitative LC assays. For convenience, the description of the present invention is divided into the following sections: I. Substrates; II. Organic layers; III. Recognition moieties; IV. Mesogenic layers; V. Patterned liquid crystals; VI. Analytes; VII. Compound libraries; VIII. Devices; and IX. Quantitation.

I. Substrates

Substrates that are useful in practicing the present invention can be made of practically any physicochemically stable material. In a preferred embodiment, the substrate material is non-reactive towards the constituents of the mesogenic layer. The substrates can be either rigid or flexible and can be either optically transparent or optically opaque. The substrates can be electrical insulators, conductors or semi-conductors. Further, the substrates can be substantially impermeable to liquids, vapors and/or gases or, alternatively, the substrates can be permeable to one or more of these classes of materials. Exemplary substrate materials include, but are not limited to, inorganic crystals, inorganic glasses, inorganic oxides, metals, organic polymers and combinations thereof.

A. Inorganic Crystal and Glasses

In some embodiments of the present invention, inorganic crystals and inorganic glasses are utilized as substrate materials (e.g., LiF, NaF, NaCl, KBr, KI, $CaF_2$, $MgF_2$, $HgF_2$, BN, $AsS_3$, ZnS, $Si_3N_4$ and the like). The crystals and glasses can be prepared by art standard techniques (See, e.g., Goodman, C. H. L., Crystal Growth Theory and Techniques, Plenum Press, New York 1974). Alternatively, the crystals can be purchased commercially (e.g., Fischer Scientific). The crystals can be the sole component of the substrate or they can be coated with one or more additional substrate components. Thus, it is within the scope of the present invention to utilize crystals coated with, for example one or more metal films or a metal film and an organic polymer. Additionally, a crystal can constitute a portion of a substrate which contacts another portion of the substrate made of a different material, or a different physical form (e.g., a glass) of the same material. Other useful substrate configurations utilizing inorganic crystals and/or glasses will be apparent to those of skill in the art.

B. Inorganic Oxides

In other embodiments of the present invention, inorganic oxides are utilized as the substrate. Inorganic oxides of use in the present invention include, for example, $Cs_2O$, $Mg(OH)_2$, $TiO_2$, $ZrO_2$, $CeO_2$, $Y_2O_3$, $Cr_2O_3$, $Fe_2O_3$, NiO, ZnO, $Al_2O_3$, $SiO_2$ (glass), quartz, $In_2O_3$, $SnO_2$, $PbO_2$ and the like. The inorganic oxides can be utilized in a variety of physical forms such as films, supported powders, glasses, crystals and the like. A substrate can consist of a single inorganic oxide or a composite of more than one inorganic oxide. For example, a composite of inorganic oxides can have a layered structure (i.e., a second oxide deposited on a first oxide) or two or more oxides can be arranged in a contiguous non-layered structure. In addition, one or more oxides can be admixed as particles of various sizes and deposited on a support such as a glass or metal sheet. Further, a layer of one or more inorganic oxides can be intercalated between two other substrate layers (e.g., metal-oxide-metal, metal-oxide-crystal).

In a presently preferred embodiment, the substrate is a rigid structure that is impermeable to liquids and gases. In this embodiment, the substrate consists of a glass plate onto which a metal, such as gold is layered by evaporative deposition. In a still further preferred embodiment, the substrate is a glass plate ($SiO_2$) onto which a first metal layer such as titanium has been layered. A layer of a second metal such as gold is then layered on top of the first metal layer.

C. Metals

In still further embodiments of the present invention, metals are utilized as substrates. The metal can be used as a crystal, a sheet or a powder. The metal can be deposited onto a backing by any method known to those of skill in the art including, but not limited to, evaporative deposition, sputtering, electroless deposition, electrolytic deposition and adsorption or deposition of preform particles of the metal including metallic nanoparticles.

Any metal that is chemically inert towards the mesogenic layer will be useful as a substrate in the present invention. Metals that are reactive or interactive towards the mesogenic layer will also be useful in the present invention. Metals that are presently preferred as substrates include, but are not limited to, gold, silver, platinum, palladium, nickel and copper. In one embodiment, more than one metal is used. The more than one metal can be present as an alloy or they can be formed into a layered "sandwich" structure, or they can be laterally adjacent to one another. In a preferred embodiment, the metal used for the substrate is gold. In a particularly preferred embodiment the metal used is gold layered on titanium.

The metal layers can be either permeable or impermeable to materials such as liquids, solutions, vapors and gases.

D. Organic Polymers

In still other embodiments of the present invention, organic polymers are utilized as substrate materials. Organic polymers useful as substrates in the present invention include polymers that are permeable to gases, liquids and molecules in solution. Other useful polymers are those that are impermeable to one or more of these same classes of compounds.

Organic polymers that form useful substrates include, for example, polyalkenes (e.g., polyethylene, polyisobutene, polybutadiene), polyacrylics (e.g., polyacrylate, polymethyl methacrylate, polycyanoacrylate), polyvinyls (e.g., polyvinyl alcohol, polyvinyl acetate, polyvinyl butyral, polyvinyl chloride), polystyrenes, polycarbonates, polyesters, polyurethanes, polyamides, polyimides, polysulfone, polysiloxanes, polyheterocycles, cellulose derivative (e.g., methyl cellulose, cellulose acetate, nitrocellulose), polysilanes, fluorinated polymers, epoxies, polyethers and phenolic resins (See, Cognard, J. ALIGNMENT OF NEMATIC LIQUID CRYSTALS AND THEIR MIXTURES, in Mol. Cryst. Liq. Cryst. 1:1-74 (1982)). Presently preferred organic polymers include polydimethylsiloxane, polyethylene, polyacrylonitrile, cellulosic materials, polycarbonates and polyvinyl pyridinium.

In a presently preferred embodiment, the substrate is permeable and it consists of a layer of gold, or gold over titanium, which is deposited on a polymeric membrane, or other material, that is permeable to liquids, vapors and/or gases. The liquids and gases can be pure compounds (e.g., chloroform, carbon monoxide) or they can be compounds that are dispersed in other molecules (e.g., aqueous protein solutions, herbicides in air, alcoholic solutions of small organic molecules). Useful permeable membranes include, but are not limited to, flexible cellulosic materials (e.g., regenerated cellulose dialysis membranes), rigid cellulosic materials (e.g., cellulose ester dialysis membranes), rigid polyvinylidene fluoride membranes, polydimethylsiloxane and track etched polycarbonate membranes.

In a further preferred embodiment, the layer of gold on the permeable membrane is itself permeable. In a still further preferred embodiment, the permeable gold layer has a thickness of about 70 Angstroms or less.

In those embodiments wherein the permeability of the substrate is not a concern and a layer of a metal film is used, the film can be as thick as is necessary for a particular application. For example, if the film is used as an electrode, the film can be thicker than in an embodiment in which it is necessary for the film to be transparent or semi-transparent to light.

Thus, in a preferred embodiment, the film is of a thickness of from about 0.01 nanometer to about 1 micrometer. In a further preferred embodiment, the film is of a thickness of from about 5 nanometers to about 100 nanometers. In yet a further preferred embodiment, the film is of a thickness of from about 10 nanometers to about 50 nanometers.

E. Substrate Surfaces

It is contemplated that the nature of the surface of the substrate has a profound effect on the anchoring of the mesogenic layer that is associated with the surface. The surface can be engineered by the use of mechanical and/or chemical techniques. The surface of each of the above enumerated substrates can be substantially smooth. Alternatively, the surface can be roughened or patterned by rubbing, etching, grooving, stretching, stressing, impacting, nanoblasting, oblique deposition or other similar techniques known to those of skill in the art. Of particular relevance is the texture of the surface that is in contact with the mesogenic compounds.

Thus, in one preferred embodiment, the substrate is glass or an organic polymer and the surface has been prepared by rubbing. Rubbing can be accomplished using virtually any material including tissues, paper, fabrics, brushes, polishing paste, etc. In a preferred embodiment, the rubbing is accomplished by use of a diamond rubbing paste. In another preferred embodiment, the face of the substrate that contacts the mesogenic compounds is a metal layer that has been obliquely deposited by evaporation. In a further preferred embodiment, the metal layer is a gold layer.

In other embodiments of the present invention, anisotropic surfaces are prepared by nanoblasting a substrate with nanometer scale beads (e.g., 1-200 nm, preferably 50-100 nm) at a defined angle of incidence (e.g., from about 5-85 degrees, preferably about 45 degrees). The nanoblasted surface can be utilized as is or can be further modified, such as by obliquely depositing gold on the surface.

In still further embodiments, the ansiotropic surfaces of the devices of the present invention are prepared by stretching an appropriate substrate. For example, polymer substrates such as polystyrene can be stretched by heating to a temperature above the glass transition temperature of the substrate, applying a tensile force, and cooling to a temperature below the glass transition temperature before removing the force.

In some embodiments, the present invention provides substrates with heterogenous features for use in the various devices and methods. In some embodiments, the heterogenity is a uniform or non-uniform gradient in topography across the surface.

For example, gold can be deposited onto a substrate at varying angles of incidence. Regions containing gold deposited at a near-normal angle of incidence will cause non-uniform anchoring of the liquid crystal, while areas in which the angle of incidence was greater than 10 degrees will uniformally orient crystals. Alternatively, the heterogeneity may be the presence of two or more distinct scales topography distributed uniformly across the substrate. It is contemplated that such substrates are useful for increasing the dynamic range of detection of analytes or for detecting the presence of analytes of a different size within a sample.

The substrate can also be patterned using techniques such as photolithography (Kleinfield et al., *J. Neurosci.* 8:4098-120 (1998)), photoetching, chemical etching, microcontact printing (Kumar et al., *Langmuir* 10:1498-511 (1994)), and chemical spotting.

The size and complexity of the pattern on the substrate is limited only by the resolution of the technique utilized and the purpose for which the pattern is intended. For example, using microcontact printing, features as small as 200 nm have been layered onto a substrate (See, Xia, Y.; Whitesides, G., *J. Am. Chem. Soc.* 117:3274-75 (1995)). Similarly, using photolithography, patterns with features as small as 1 μm have been produced (See, Hickman et al., *J. Vac. Sci. Technol.* 12:607-16 (1994)). Patterns which are useful in the present invention include those which comprise features such as wells, enclosures, partitions, recesses, inlets, outlets, channels, troughs, diffraction gratings and the like.

In a presently preferred embodiment, the patterning is used to produce a substrate having a plurality of adjacent wells, wherein each of the wells is isolated from the other wells by a raised wall or partition and the wells do not fluidically communicate. Thus, an analyte, or other substance, placed in a particular well remains substantially confined to that well. In another preferred embodiment, the patterning allows the creation of channels through the device whereby an analyte can enter and/or exit the device.

The pattern can be printed directly onto the substrate or, alternatively, a "lift off" technique can be utilized. In the lift off technique, a patterned resist is laid onto the substrate, an organic layer is laid down in those areas not covered by the resist and the resist is subsequently removed. Resists appropriate for use with the substrates of the present invention are known to those of skill in the art (See, e.g., Kleinfield et al., *J. Neurosci.* 8:4098-120 (1998)). Following removal of the photoresist, a second organic layer, having a structure different from the first organic layer, can be bonded to the substrate on those areas initially covered by the resist. Using this technique, substrates with patterns having regions of different chemical characteristics can be produced. Thus, for example, a pattern having an array of adjacent wells can be created by varying the hydrophobicity/hydrophilicity, charge and other chemical characteristics of the pattern constituents. In one embodiment, hydrophilic compounds can be confined to individual wells by patterning walls using hydrophobic materials. Similarly, positively or negatively charged compounds can be confined to wells having walls made of compounds with charges similar to those of the confined compounds. Similar substrate configurations are accessible through microprinting a layer with the desired characteristics directly onto the substrate (See, Mrkish, M.; Whitesides, G. M., *Ann. Rev. Biophys. Biomol. Struct.* 25:55-78 (1996)).

In yet another preferred embodiment, the patterned substrate controls the anchoring alignment of the liquid crystal. In a particularly preferred embodiment, the substrate is patterned with an organic compound that forms a self-assembled monolayer. In this embodiment, the organic layer controls the azimuthal orientation and/or polar orientation of a supported mesogenic layer.

F. Detection of Non-Specific Adsorption of Analytes

In some embodiments, substrates that uniformly orient mesogens are utilized to non-specifically bind analytes such as polypeptides or polynucleotides. Accordingly, in some embodiments, the present invention provides methods for detecting molecules resolved by gel electophoresis, capillary electrophoreis, chromatography, and other separation technologies. Substrates suitable for detection of nonspecific binding include rubbed PVDF membranes, rubbed nitrocellulose, and rubbed cellulose nitrate. In preferred embodiments, proteins or nucleic acids from an electrophoretic gel are transferred to the substrate by application of an electric field in an appropriate buffer (e.g., Western, Southern, or Northern blotting conditions). After transfer of the molecules to the surface, a mesogen layer and optionally a second substrate that uniformly orients mesogens are applied as described in more detail herein so that the non-specific binding can be detected. In addition to the analysis of resolved biomolecules, it is contemplated that analysis of non-specific binding is also useful quality control of manufactured biomolecules. In other embodiments of the invention, an obliquely deposited film of metal that supports an organic layer is used. A still preferred embodiment would be a self-assembled monolayer formed from an organosulfur compounds on the surface of a gold or silver film. In some cases, the self-assembled monolayer can be patterned with regions possessing different physical properties to affect the separation of analytes from a mixture by their interaction with the surface. A preferred pattern would be one in which their exists a continuous gradient in properties across a surface.

II. Organic Layers

In addition to the ability of a substrate to anchor a mesogenic layer, an organic layer attached to the substrate is similarly able to provide such anchoring. A wide range of organic layers can be used in conjunction with the present invention. These include, but are not limited to, organic layers formed from organosulfur compounds (including thiols and disulfides), organosilanes, amphiphilic molecules, cyclodextrins, polyols (e.g., poly(ethyleneglycol), poly(propyleneglycol), fullerenes, and biomolecules.

A. Anchoring

An organic layer that is bound to, supported on or adsorbed onto, the surface of the substrate can anchor a mesogenic layer. As used herein, the term "anchoring" refers to the set of orientations adopted by the molecules in the mesogenic phase. The mesogenic layer will adopt particular orientations while minimizing the free energy of the interface between the organic layer and the mesogenic layer. The orientation of the mesogenic layer is referred to as an "anchoring direction." A number of anchoring directions are possible.

It is contemplated that the particular anchoring direction adopted will depend upon the nature of the mesogenic layer, the organic layer and the substrate. Anchoring directions of use in the present invention include, for example, conical anchoring, degenerate anchoring, homeotropic anchoring, multistable anchoring, planar anchoring and tilted anchoring. Planar anchoring and homeotropic anchoring are preferred with planar anchoring being most preferred.

The anchoring of mesogenic compounds by surfaces has been extensively studied for a large number of systems (See, for example, Jerome, *Rep. Prog. Phys.* 54:391-451 (1991)). The anchoring of a mesogenic substance by a surface is specified, in general, by the orientation of the director of the bulk phase of the mesogenic layer. The orientation of the director, relative to the surface, is described by a polar angle (measured from the normal of the surface) and an azimuthal angle (measured in the plane of the surface).

Control of the anchoring of mesogens has been largely based on the use of organic surfaces prepared by coating surface-active molecules or polymer films on inorganic (e.g., silicon oxide) substrates followed by surface treatments such as rubbing. Other systems which have been found useful include surfaces prepared through the reactions of organosilanes with various substrates (See, for example, Yang et al., In MICROCHEMISTRY: SPECTROSCOPY AND CHEMISTRY IN SMALL DOMAINS; Masuhara et al., Eds.; North-Holland, Amsterdam, 1994; p. 441).

Molecularly designed surfaces formed by organic layers on a substrate can be used to control both the azimuthal and polar orientations of a supported mesogenic layer. SAMs can be patterned on a surface. For example, patterned organic layers made from $CH_3(CH_2)_{14}SH$ and $CH_3(CH_2)_{15}SH$ on obliquely deposited gold produce a supported mesogenic layer which is twisted 90°. Other anchoring modes are readily accessible by varying the chain length and the number of species of the organic layer constituents (See, Gupta and Abbott, *Science* 276:1533-1536 (1997)).

Transitions between anchoring modes have been obtained on a series of organic layers by varying the structure of the organic layer. The structural features which have been found to affect the anchoring of mesogenic compounds include, for example, the density of molecules within the organic layer, the size and shape of the molecules constituting the organic layer and the number of individual layers making up the bulk organic layer.

The density of the organic layer on the substrate has been shown to have an effect on the mode of mesogen anchoring. For example, transitions between homeotropic and degenerate anchorings have been obtained on surfactant monolayers by varying the density of the monolayers (See, Proust et al., *Solid State Commun.* 11:1227-30 (1972)). Thus, it is within the scope of the present invention to tailor the anchoring mode of a mesogen by controlling the density of the organic layer on the substrate.

The molecular structure, size and shape of the individual molecules making up the organic layer also affects the anchoring mode. For example, it has been demonstrated that varying the length of the aliphatic chains of surfactants on a substrate can also induce anchoring transitions; with long chains, a homeotropic anchoring is obtained while with short chains, a conical anchoring is obtained with the tilt angle 0 increasing as the chain becomes shorter (See, e.g., Porte, J. *Physique* 37:1245-52 (1976)). Additionally, recent reports have demonstrated that the polar angle of the mesogenic phase can be controlled by the choice of the constituents of the organic layer. See, Gupta and Abbott, *Langmuir* 12:2587-2593 (1996). Thus, it is within the scope of the present invention to engineer the magnitude of the anchoring shift as well as the type of shift by the judicious choice of organic layer constituents.

Biomolecules can also be used as organic layers. (see Seung-Ryeol Kim, Rahul R. Shah, and Nicholas L. Abbott; Orientations of Liquid Crystals on Mechanically Rubbed Films of Bovine Serum Albumin: A Possible Substrate for Biomolecular Assays Based on Liquid Crystals, Analytical Chemistry; 2000; 72(19); 4646-4653.). A preferred embodiment when using biomolecules as organic layers is based on the mechanical rubbing of the organic layer with a fabric cloth following chemical immobilization of the organic layer on the surface of a substrate.

A wide variety of organic layers are useful in practicing the present invention. These organic layers can comprise monolayers, bilayers and multilayers. Furthermore, the organic layers can be attached by covalent bonds, ionic bonds, physisorption, chemisorption and the like, including, but not limited to, hydrophobic interactions, hydrophilic interactions, van der Waals interactions and the like.

In a presently preferred embodiment, organic layers which form selfassembled monolayers are used. The use of self-assembled monolayers (SAMs) formed from alkanethiols on thin, semitransparent films of gold in studies on the anchoring of liquid crystals on surfaces has been reported (See, Drawhorn and Abbott, *J. Phys. Chem.* 45:16511 (1995)). The principal result of that work was the demonstration that SAMs formed from n-alkanethiols with long ($CH3(CH2)_{15}SH$) and short ($CH_3(CH_2)_4SH$ or $CH3(CH_2)_9SH$) aliphatic chains can homeotropically anchor mesogens. In contrast, single-component SAMs caused non-uniform, planar, or tilted anchoring at room temperature.

In the discussion that follows, self-assembled monolayers are utilized as an exemplary organic layer. This use is not intended to be limiting. It will be understood that the various configurations of the self-assembled monolayers and their methods of synthesis, binding properties and other characteristics are equally applicable to each of the organic layers of use in the present invention.

B. Self-Assembled Monolayers

Self-assembled monolayers are generally depicted as an assembly of organized, closely packed linear molecules. There are two widely-used methods to deposit molecular monolayers on solid substrates: Langmuir-Blodgett transfer and self-assembly. Additional methods include techniques such as depositing a vapor of the monolayer precursor onto a substrate surface and the layer-by-layer deposition of polymers and polyelectrolytes from solution (Guy Ladam, Pierre Schaaf, Frédéric J. G. Cuisinier, Gero Decher, and Jean-Claude Voegel; Protein Adsorption onto Auto-Assembled Polyelectrolyte Films, Langmuir; 2001; 17(3); 878-882).

The composition of a layer of a SAM useful in the present invention can be varied over a wide range of compound structures and molar ratios. In one embodiment, the SAM is formed from only one compound. In a presently preferred embodiment, the SAM is formed from two or more components. In another preferred embodiment, when two or more components are used, one component is a long-chain hydrocarbon having a chain length of between 10 and 25 carbons and a second component is a short-chain hydrocarbon having a chain length of between 1 and 9 carbon atoms. In particularly preferred embodiments, the SAM is formed from $CH_3(CH_2)_{15}SH$ and $CH_3(CH_2)_4SH$ or $CH_3(CH_2)_{15}SH$ and $CH_3(CH_2)_9SH$. In any of the above-described embodiments, the carbon chains can be functionalized at the ω-terminus (e.g., $NH_2$, COOH, OH, CN), at internal positions of the chain (e.g., aza, oxa, thia) or at both the w-terminus and internal positions of the chain.

The mesogenic layer can be layered on top of one SAM layer or it can be sandwiched between two SAM layers. In those embodiments in which the mesogenic layer is sandwiched between two SAMs, a second substrate, optionally substantially identical in composition to that bearing the SAM can be layered on top of the mesogenic layer. Alternatively a compositionally different substrate can be layered on top of the mesogenic layer. In a preferred embodiment, the second substrate is permeable. In yet another preferred embodiment two substrates are used, but only one of the substrates has an attached organic layer.

When the mesogenic layer is sandwiched between two layers of SAMs several compositional permutations of the layers of SAMs are available. For example, in one embodiment, the first organic layer and the second organic layer have substantially identical compositions and both of the organic layers bear an attached recognition moiety. A variation on this embodiment utilizes first and second organic layers with substantially similar compositions, wherein only one of the layers bears a recognition moiety.

In another embodiment, the first and second organic layers have substantially different compositions and only one of the organic layers has an attached recognition moiety. In a further embodiment, the first organic layer and said second organic layer have substantially different compositions and both of the organic layers have an attached recognition moiety.

In a presently preferred embodiment, the organic layers have substantially identical compositions and one or both of the organic layers have attached thereto a recognition moiety.

A recognition moiety can be attached to the surface of a SAM by any of a large number of art-known attachment methods. In one preferred embodiment, a reactive SAM component is attached to the substrate and the recognition moiety is subsequently bound to the SAM component via the reactive group on the component and a group of complementary reactivity on the recognition moiety (See, e.g., Hegner et al. *Biophys. J.* 70:2052-2066 (1996)). In another preferred embodiment, the recognition moiety is attached to the SAM component prior to immobilizing the SAM component on the substrate surface: the recognition moiety-SAM component cassette is then attached to the substrate. In a still further preferred embodiment, the recognition moiety is attached to the substrate via a displacement reaction. In this embodiment, the SAM is preformed and then a fraction of the SAM components are displaced by a recognition moiety or a SAM component bearing a recognition moiety.

C. Functionalized SAMs

The discussion that follows focuses on the attachment of a reactive SAM component to the substrate surface. This focus is for convenience only and one of skill in the art will understand that the discussion is equally applicable to embodiments in which the SAM component-recognition moiety is preformed prior to its attachment to the substrate. As used herein, "reactive SAM components" refers to components which have a functional group available for reaction with a recognition moiety or other species following the attachment of the component to the substrate.

Currently favored classes of reactions available with reactive SAM components are those that proceed under relatively mild conditions. These include, but are not limited to nucleophilic substitutions (e.g., reactions of amines and alcohols with acyl halides), electrophilic substitutions (e.g., enamine reactions) and additions to carbon-carbon and carbon-heteroatom multiple bonds (e.g., Michael reaction, Diels-Alder addition). These and other useful reactions are discussed in March, ADVANCED ORGANIC CHEMISTRY, Third Ed., John Wiley & Sons, New York, 1985.

According to the present invention, a substrate's surface is functionalized with SAM, components and other species by covalently binding a reactive SAM component to the substrate surface in such a way as to derivatize the substrate surface with a plurality of available reactive functional groups. Reactive groups which can be used in practicing the present invention include, for example, amines, hydroxyl groups, carboxylic acids, carboxylic acid derivatives, alkenes, sulfhydryls, siloxanes, etc.

A wide variety of reaction types are available for the functionalization of a substrate surface. For example, substrates constructed of a plastic such as polypropylene, can be surface derivatized by chromic acid oxidation, and subsequently converted to hydroxylated or aminomethylated surfaces. Substrates made from highly crosslinked divinylbenzene can be surface derivatized by chloromethylation and subsequent functional group manipulation. Additionally, functionalized substrates can be made from etched, reduced polytetrafluoroethylene.

When the substrates are constructed of a siliaceous material such as glass, the surface can be derivatized by reacting the surface Si—OH, Si0-H, and/or Si—Si groups with a functionalizing reagent. When the substrate is made of a metal film, the surface can be derivatized with a material displaying avidity for that metal.

In a preferred embodiment, wherein the substrates are made from glass, the covalent bonding of the reactive group to the glass surface is achieved by conversion of groups on the substrate's surface by a silicon modifying reagent such as:

(1)

where R is an alkyl group, such as methyl or ethyl, $R^1$ is a linking group between silicon and X and X is a reactive group or a protected reactive group. The reactive group can also be a recognition moiety as discussed below. Silane derivatives having halogens or other leaving groups beside the displayed alkoxy groups are also useful in the present invention.

A number of siloxane functionalizing reagents can be used, for example:

1. Hydroxyalkyl siloxanes (Silylate surface, functionalize with diborane, and $H_2O_2$ to oxidize the alcohol)
   a. allyl trichlorosilane→→3-hydroxypropyl
   b. 7-oct-1-enyl trichlorosilane→→8-hydroxyoctyl
2. Diol (dihydroxyalkyl) siloxanes (silylate surface and hydrolyze to diol)
   a. (glycidyl trimethoxysilane→→(2,3-dihydroxypropyloxy)propyl
3. Aminoalkyl siloxanes (amines requiring no intermediate functionalizing step).
   a. 3-aminopropyl trimethoxysilane→aminopropyl
4. Dimeric secondary aminoalkyl siloxanes
   a. bis (3-trimethoxysilylpropyl) amine→bis(silyloxylpropyl)amine.

It will be apparent to those of skill in the art that an array of similarly useful functionalizing chemistries are available when SAM components other than siloxanes are used. Thus, for example similarly functionalized alkyl thiols can be attached to metal films and subsequently reacted to produce the functional groups such as those exemplified above.

In another preferred embodiment, the substrate is at least partially a metal film, such as a gold film, and the reactive group is tethered to the metal surface by an agent displaying avidity for that surface. In a presently preferred embodiment, the substrate is at least partially a gold film and the group which reacts with the metal surface comprises a thiol, sulfide or disulfide such as:

(2)

$R^2$ is a linking group between sulfur and $X^2$ and $X^2$ is a reactive group or a protected reactive group. $X^2$ can also be a recognition moiety as discussed below. Y is a member selected from the group consisting of H, $R^3$ and $R^3$—S—, wherein $R^2$ and $R^3$ are independently selected. When $R^2$ and $R^3$ are the same, symmetrical sulfides and disulfides result, and when they are different, asymmetrical sulfides and disulfides result.

A large number of functionalized thiols, sulfides and disulfides are commercially available (Aldrich Chemical Co., St. Louis). Additionally, those of skill in the art have available to them a manifold of synthetic routes with which to produce additional such molecules. For example, amine-functionalized thiols can be produced from the corresponding halo-amines, halo-carboxylic acids, etc. by reaction of these halo precursors with sodium sulfhydride. See, e.g., Reid, ORGANIC CHEMISTRY of BIVALENT SULFUR, VOL 1, pp. 21-29, 32-35, vol. 5, pp. 27-34, Chemical Publishing Co., New York, 1.958, 1963. Additionally, functionalized sulfides can be prepared via alkylthio-de-halogenation with a mercaptan salt (See, Reid, ORGANIC CHEMISTRY OF BIVALENT SULFUR, vol. 2, pp. 16-21, 24-29, vol. 3, pp. 11-14, Chemical Publishing Co., New York, 1960). Other methods for producing compounds useful in practicing the present invention will be apparent to those of skill in the art.

In another preferred embodiment, the functionalizing reagent provides for more than one reactive group per each reagent molecule. Using reagents such as Compound 3, below, each reactive site on the substrate surface is, in essence, "amplified" to two or more functional groups:

$$(RO)_3-Si-R^2-(X^2)_n \qquad (3)$$

where R is an alkyl group, such as methyl, $R^2$ is a linking group between silicon and $X^2$, $X^2$ is a reactive group or a protected reactive group and n is an integer between 2 and 50, and more preferably between 2 and 20.

Similar amplifying molecules are also of use in those embodiments wherein the substrate is at least partially a metal film. In these embodiments the group that reacts with the metal surface comprises a thiol, sulfide or disulfide such as in Formula (4):

$$Y-S-R^2-(X^2)_n \qquad (4)$$

As discussed above, $R^2$ is a linking group between sulfur and $X^2$ and $X^2$ is a reactive group or a protected reactive group. $X^2$ can also be a recognition moiety. Y is a member selected from the group consisting of H, $R^3$ and $R^3-S-$, wherein $R^2$ and $R^3$ are independently selected.

R groups of use for $R^1$, $R^2$ and $R^3$ in the above described embodiments of the present invention include, but are not limited to, alkyl, substituted alkyl, aryl, arylalkyl, substituted aryl, substituted arylalkyl, acyl, halogen, hydroxy, amino, alkylamino, acylamino, alkoxy, acyloxy, aryloxy, aryloxyalkyl, mercapto, saturated cyclic hydrocarbon, unsaturated cyclic hydrocarbon, heteroaryl, heteroarylalkyl, substituted heteroaryl, substituted heteroarylalkyl, heterocyclic, substituted heterocyclic and heterocyclicalkyl groups.

In each of Formulae 1-4, above, each of $R^1$, $R^2$ and $R^3$ are either stable or they can be cleaved by chemical or photochemical reactions. For example, R groups comprising ester or disulfide bonds can be cleaved by hydrolysis and reduction, respectively. Also within the scope of the present invention is the use of R groups, which are cleaved by light such as, for example, nitrobenzyl derivatives, phenacyl groups, benzoin esters, etc. Other such cleaveable groups are well-known to those of skill in the art.

In another preferred embodiment, the organosulfur compound is partially or entirely halogenated. An example of compounds useful in this embodiment include:

$$X^1Q_2C(CQ^1_2)_mZ^1(CQ^2_2)_nSH \qquad (5)$$

wherein, $X^1$ is a member selected from the group consisting of H, halogen reactive groups and protected reactive groups. Reactive groups can also be recognition moieties as discussed below. Q, $Q^1$ and $Q^2$ are independently members selected from the group consisting of H and halogen. $Z^1$ is a member selected from the group consisting of $-CQ_2-$, $-CQ^1_2-$, $-CQ^2_2-$, $-O-$, $-S-$, $NR^4-$, $-C(O)NR^4$ and $R^4NC(O0-$, in which $R^4$ is a member selected from the group consisting of H, alkyl, substituted alkyl, aryl, substituted aryl, heteroaryl and heterocyclic groups and m and n are independently a number between 0 and 40.

In yet another preferred embodiment, the organic layer comprises a compound according to Formula 5 above, in which Q, $Q^1$ and $Q^2$ are independently members selected from the group consisting of H and fluorine. In a still further preferred embodiment, the organic layer comprises compounds having a structure according to Formulae (6) and (7):

$$CF_3(CF_2)_mZ^1(CH_2)_nSH \qquad (6)$$

$$CF_3(CF_2)_oZ^2(CH_2)_pSH \qquad (7)$$

wherein, $Z^1$ and $Z^2$ are members independently selected from the group consisting of $-CH_2-$, $-O-$, $-S-$, $NR^4$, $-C(O)NR^4$ and $R^4NC(O)-$ in which $R^4$ is a member selected from the group consisting of H, alkyl, substituted alkyl, aryl, substituted aryl, heteroaryl and heterocyclic groups. In a presently preferred embodiment, the Z groups of adjacent molecules participate in either an attractive (e.g., hydrogen bonding) or repulsive (e.g., van der Waals) interaction.

In Formula 7, m is a number between 0 and 40, n is a number between 0 and 40, o is a number between 0 and 40 and p is a number between 0 and 40.

In a further preferred embodiment, the compounds of Formulae 6 and 7 are used in conjunction with an organosulfur compound, either halogentated or unhalogenated, that bears a recognition moiety.

When the organic layer is formed from a halogenated organosulfur compound, the organic layer can comprise a single halogenated compound or more than one halogenated compound having different structures. Additionally, these layers can comprise a non-halogenated organosulfur compound.

The reactive functional groups ($X^1$ and $X^2$) are, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups which can be converted to disulfides or reacted with acyl halides;

(h) amine or sulfhydryl groups which can be, for example, acylated or alkylated;

(i) alkenes which can undergo, for example, cycloadditions, acylation, Michael addition, etc; and (j) epoxides which can react with, for example, amines and hydroxyl compounds.

The reactive moieties can also be recognition moieties. The nature of these groups is discussed in greater detail below.

The reactive functional groups can be chosen such that they do not participate in, or interfere with, the reaction controlling the attachment of the functionalized SAM component onto the substrate's surface. Alternatively, the reactive functional group can be protected from participating in the reaction by the presence of a protecting group. Those of skill in the art will understand how to protect a particular functional group from interfering with a chosen set of reaction conditions. For examples of useful protecting groups, see Greene et al., PROTECTIVE GROUPS IN ORGANIC SYNTHESIS, John Wiley & Sons, New York, 1991.

In a preferred embodiment, the SAM component bearing the recognition moiety is attached directly and essentially irreversibly via a "stable bond" to the surface of the substrate. A "stable bond", as used herein, is a bond which maintains its chemical integrity over a wide range of conditions (e.g., amide, carbamate, carbon-carbon, ether, etc.). In another preferred embodiment, the SAM component bearing the recognition moiety is attached to the substrate surface by a "cleaveable bond". A "cleaveable bond", as used herein, is a bond that is designed to undergo scission under conditions that do not degrade other bonds in the recognition moiety-analyte complex. Cleaveable bonds include, but are not limited to, disulfide, imine, carbonate and ester bonds.

In certain embodiments, it is advantageous to have the recognition moiety attached to a SAM component having a structure that is different than that of the constituents of the bulk SAM. In this embodiment, the group to which the recognition moiety is bound is referred to as a "spacer arm" or "spacer." Using such spacer arms, the properties of the SAM adjacent to the recognition moiety can be controlled. Properties that are usefully controlled include, for example, hydrophobicity, hydrophilicity, surface-activity and the distance of the recognition moiety from the plane of the substrate and/or the SAM. For example, in a SAM composed of alkanethiols, the recognition moiety can be attached to the substrate or the surface of the SAM via an amine terminated poly(ethyleneglycol). Numerous other combinations of spacer arms and SAMs are accessible to those of skill in the art.

The hydrophilicity of the substrate surface can be enhanced by reaction with polar molecules such as amine-, hydroxyl- and polyhydroxylcontaining molecules. Representative examples include, but are not limited to, polylysine, polyethyleneimine, poly(ethyleneglycol) and poly(propyleneglycol). Suitable functionalization chemistries and strategies for these compounds are known in the art (See, for example, Dunn, R. L., et al., Eds. POLYMERIC DRUGS AND DRUG DELIVERY SYSTEMS, ACS Symposium Series Vol. 469, American Chemical Society, Washington, D.C. 1991).

The hydrophobicity of the substrate surface can be modulated by using a hydrophobic spacer arm such as, for example, long chain diamines, longchain thiols, $\alpha$, $\omega$-amino acids, etc. Representative hydrophobic spacers include, but are not limited to, 1,6-hexanediamine, 1,8-octanediamine, 6-aminohexanoic acid and 8-aminooctanoic acid.

The substrate surface can also be made surface-active by attaching to the substrate surface a spacer that has surfactant properties. Compounds useful for this purpose include, for example, aminated or hydroxylated detergent molecules such as, for example, 1-aminododecanoic acid.

In another embodiment, the spacer serves to distance the recognition moiety from the substrate or SAM. Spacers with this characteristic have several uses. For example, a recognition moiety held too closely to the substrate or SAM surface may not react with incoming analyte, or it may react unacceptably slowly. When an analyte is itself sterically demanding, the reaction leading to recognition moiety-analyte complex formation can be undesirably slowed, or not occur at all, due to the monolithic substrate hindering the approach of the two components.

In another embodiment, the physicochemical characteristics (e.g., hydrophobicity, hydrophilicity, surface activity, conformation) of the substrate surface and/or SAM are altered by attaching a monovalent moiety which is different in composition than the constituents of the bulk SAM and which does not bear a recognition moiety. As used herein, "monovalent moiety" refers to organic molecules with only one reactive functional group. This functional group attaches the molecule to the substrate. "Monovalent moieties" are to be contrasted with the bifunctional "spacer" groups described above. Such monovalent groups are used to modify the hydrophilicity, hydrophobicity, binding characteristics, etc. of the substrate surface. Examples of groups useful for this purpose include long chain alcohols, amines, fatty acids, fatty acid derivatives, poly(ethyleneglycol) monomethyl ethers, etc.

When two or more structurally distinct moieties are used as components of the SAMs, the components can be contacted with the substrate as a mixture of SAM components or, alternatively, the components can be added individually. In those embodiments in which the SAM components are added as a mixture, the mole ratio of a mixture of the components in solution results in the same ratio in the mixed SAM. Depending on the manner in which the SAM is assembled, the two components do not phase segregate into islands (See, Bain and Whitesides, *J. Am. Chem. Soc.* 111:7164 (1989)). This feature of SAMs can be used to immobilize recognition moieties or bulky modifying groups in such a manner that certain interactions, such as steric hindrance, between these molecules is minimized.

The individual components of the SAMs can also be bound to the substrate in a sequential manner. Thus, in one embodiment, a first SAM component is attached to the substrate's surface by "underlabeling" the surface functional groups with less than a stoichiometric equivalent of the first component. The first component can be a SAM component liked to a terminal reactive group or recognition group, a spacer arm or a monovalent moiety. Subsequently, the second component is contacted with the substrate. This second component can either be added in stoichiometric equivalence, stoichiometric excess or can again be used to underlabel to leave sites open for a third component.

D. Detection of Non-Specific Adsorption of Analytes

In some embodiments, substrates prepared with an organic layer are utilized to non-specifically bind analytes such as polypeptides or polynucleotides. Accordingly, in some embodiments, the present invention provides methods for detecting molecules resolved by gel electrophoresis, capillary electrophoreis, chromatography, and other separation technologies. In some embodiments, the surface of the substrate is coated with a monolayer that possesses a property useful for non-specific adsorption of molecules or particular classes of molecules. For example, in some embodiments, a gold surface is coated with a hydrophobic monolayer (e.g., formed from hexadecanethiol) and a sample containing proteins is contacted with the hydrophobic monolayer under conditions such that the proteins in the sample associate with the hydrophobic monolayer. In preferred embodiments, proteins from an electrophoretic gel are transferred to the hydrophobic surface by application of an electric field in an appropriate buffer (e.g., Western blotting conditions). In other embodiments, the gold surface is coated a positively charged monolayer (e.g., formed from $HS(CH_2)_8N^+(CH_3)_3$) that binds negatively charged polynucleotides (e.g., DNA or RNA). In still further embodiments, the surface is prepared with patterned monolayers with different functionalities (e.g., positive or negative charge where the negative charged regions are formed using $SH(CH_2)_2SO_3^-$) so that molecules with different properties (e.g., isolectric point at a given pH) bind to different areas of the surface. After transfer of the molecules to the surface, a mesogen layer and optionally a second substrate that uniformly orients mesogens are applied as described in more detail herein so that the non-specific binding can be detected. Mixed monolayers formed from positively charged, negatively charged and electrically neutral species can be used to tune the properties of the surface via variation of the composition of the mixed monolayer. These mixed monolayers can be prepared by co-adsorption, sequential adsorption or displacement on the surface.

III. Recognition Moieties

In some embodiments of the present invention, a "recognition moiety" attached to or associated with the substrate is utilized to bind to or otherwise interact with another molecule or molecules (e.g., analytes). For example, in some embodiments, recognition moieties are attached to either ω-functionalized spacer arms or ω-functionalized SAM components, which are in turn attached to or associated with the substrate. Furthermore, a recognition moiety can be presented by a polymer surface (e.g., a rubbed polymer surface).

In some preferred embodiments, the recognition moiety comprises an organic functional group. In presently preferred embodiments, the organic functional group is a member selected from the group consisting of amines, carboxylic acids, drugs, chelating agents, crown ethers, cyclodextrins or a combination thereof.

In another preferred embodiment, the recognition moiety is a biomolecule. In still further preferred embodiments, the biomolecule is a protein, antigen binding protein, peptide, nucleic acid (e.g., single nucleotides or nucleosides, oligonucleotides, polynucleotides and single- and higher-stranded nucleic acids) or a combination thereof. In a presently preferred embodiment, the recognition moiety is biotin. In some embodiments of the present invention, the recognition moiety is an antigen binding protein. Such antigen binding proteins include, but are not limited to polyclonal, monoclonal, chimeric, single chain, Fab fragments, and Fab expression libraries.

Various procedures known in the art may be used for the production of polyclonal antibodies. For the production of antibody, various host animals, including but not limited to rabbits, mice, rats, sheep, goats, etc., can be immunized by injection with the peptide corresponding to an epitope. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies, it is contemplated that any technique that provides for the production of antibody molecules by continuous cell lines in culture will find use with the present invention (See e.g., Harlow and Lane, *Antibodies: A Laboratory Manual*, Cold Spring Harbor Laboratory Press, Cold Spring Harbor, N.Y.). These include but are not limited to the hybridoma technique originally developed by Köhler and Milstein (Köhler and Milstein, Nature 256:495-497 [1975]), as well as the trioma technique, the human B-cell hybridoma technique (See e.g., Kozbor et al., Immunol. Tod., 4:72 [1983]), and the EBV-hybridoma technique to produce human monoclonal antibodies (Cole et al., in *Monoclonal Antibodies and Cancer Therapy*, Alan R. Liss, Inc., pp. 77-96 [1985]).

In addition, it is contemplated that techniques described for the production of single chain antibodies (U.S. Pat. No. 4,946,778; herein incorporated by reference) will find use in producing specific single chain antibodies that serve as recognition moieties. Furthermore, it is contemplated that any technique suitable for producing antibody fragments will find use in generating antibody fragments that are useful recognition moieties. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent. In still further embodiments, the recognition moiety comprises a phage displaying an antigen binding protein.

In some embodiments where the recognition moiety is a polynucleotide or polypeptide, a plurality of recognition moieties are arrayed on the substrates using photo activated chemistry, microcontact printing, and ink-jet printing. In particularly preferred embodiments, photolithography is utilized (See e.g., U.S. Pat. Nos. 6,045,996; 5,925,525; and 5,858,659; each of which is herein incorporated by reference). Using a series of photolithographic masks to define substrate exposure sites, followed by specific chemical synthesis steps, the process constructs high-density arrays of oligonucleotides, with each probe in a predefined position in the array. Multiple probe arrays are synthesized simultaneously on, for example, a large glass wafer. The wafers are then diced, and individual probe arrays are packaged in injection-molded plastic cartridges, which protect them from the environment and serve as chambers for hybridization.

In other embodiments, nucleic acid recognition moieties are electronically captured on a suitable substrate (See e.g., U.S. Pat. Nos. 6,017,696; 6,068,818; and 6,051,380; each of which are herein incorporated by reference). Through the use of microelectronics, this technology enables the active movement and concentration of charged molecules to and from designated test sites on its semiconductor microchip. DNA capture probes unique to a given target are electronically placed at, or "addressed" to, specific sites on the microchip. Since DNA has a strong negative charge, it can be electronically moved to an area of positive charge.

In still further embodiments, recognition moieties are arrayed on a suitable substrate by utilizing differences in surface tension (See e.g., U.S. Pat. Nos. 6,001,311; 5,985,551; and 5,474,796; each of which is herein incorporated by reference). This technology is based on the fact that fluids can be segregated on a flat surface by differences in surface tension that have been imparted by chemical coatings. Once so segregated, oligonucleotide probes are synthesized directly on the chip by ink-jet printing of reagents. The array with its reaction sites defined by surface tension is mounted on a X/Y translation stage under a set of four piezoelectric nozzles, one for each of the four standard DNA bases. The translation stage moves along each of the rows of the array and the appropriate reagent is delivered to each of the reaction site. For example, the A amidite is delivered only to the sites where amidite A is to be coupled during that synthesis step and so on. Common reagents and washes are delivered by flooding the entire surface and then removing them by spinning.

In still further embodiments, recognition moieties are spotted onto a suitable substrate. Such spotting can be done by hand with a capillary tube or micropipette, or by an automated spotting apparatus such as those available from Affymetrix and Gilson (See e.g., U.S. Pat. Nos. 5,601,980; 6,242,266; 6,040,193; and 5,700,637; each of which is incorporated herein by reference).

When the recognition moiety is an amine, in preferred embodiments, the recognition moiety will interact with a structure on the analyte which reacts by binding to the amine (e.g., carbonyl groups, alkylhalo groups). In another preferred embodiment, the amine is protonated by an acidic moiety on the analyte of interest (e.g., carboxylic acid, sulfonic acid).

In certain preferred embodiments, when the recognition moiety is a carboxylic acid, the recognition moiety will interact with the analyte by complexation (e.g., metal ions). In still other preferred embodiments, the carboxylic acids will protonate a basic group on the analyte (e.g. amine).

In another preferred embodiment, the recognition moiety is a drug moiety. The drug moieties can be agents already accepted for clinical use or they can be drugs whose use is experimental, or whose activity or mechanism of action is under investigation. The drug moieties can have a proven action in a given disease state or can be only hypothesized to show desirable action in a given disease state. In a preferred embodiment, the drug moieties are compounds that are being screened for their ability to interact with an analyte of choice. As such, drug moieties that are useful in practicing the instant invention include drugs from a broad range of drug classes having a variety of pharmacological activities.

Classes of useful agents include, for example, non-steroidal anti-inflammatory drugs (NSAIDS). The MAIDS can, for example, be selected from the following categories: (e.g., propionic acid derivatives, acetic acid derivatives, fenamic acid derivatives, biphenylcarboxylic acid derivatives and oxicams); steroidal anti-inflammatory drugs including hydrocortisone and the like; antihistaminic drugs (e.g., chlorpheniranune, triprolidine); antitussive drugs (e.g., dextromethorphan, codeine, carmiphen and carbetapentane); antipruritic drugs (e.g., methidilizine and trimeprizine); anticholinergic drugs (e.g., scopolamine, atropine, homatropine, levodopa); anti-emetic and antinauseant drugs (e.g., cyclizine, meclizine, chlorpromazine, buclizine); anorexic drugs (e.g., benzphetamine, phentermine, chlorphentermine, fenfluramine); central stimulant drugs (e.g., amphetamine, methamphetamine, dextroamphetamine and methylphenidate); antiarrhythmic drugs (e.g., propanolol, procainamide, disopyraminde, quinidine, encainide); P-adrenergic blocker drugs (e.g., metoprolol, acebutolol, betaxolol, labetalol and timolol); cardiotonic drugs (e.g., milrinone, amrinone and dobutamine); antihypertensive drugs (e.g., enalapril, clonidine, hydralazine, minoxidil, guanadrel, guanethidine); diuretic drugs (e.g., amiloride and hydrochlorothiazide); vasodilator drugs (e.g., diltazem, amiodarone, isosuprine, nylidrin, tolazoline and verapamil); vasoconstrictor drugs (e.g., dihydroergotamine, ergotamine and methylsergide); antiulcer drugs (e.g., ranitidine and cimetidine); anesthetic drugs (e.g., lidocaine, bupivacaine, chlorprocaine, dibucaine); antidepressant drugs (e.g., imipramine, desipramine, amitryptiline, nortryptiline); tranquilizer and sedative drugs (e.g., chlordiazepoxide, benacytyzine, benzquinamide, flurazepam, hydroxyzine, loxapine and promazine); antipsychotic drugs (e.g., chlorprothixene, fluphenazine, haloperidol, molindone, thioridazine and trifluoperazine); antimicrobial drugs (antibacterial, antifungal, antiprotozoal and antiviral drugs).

Antimicrobial drugs which are preferred for incorporation into the present composition include, for example, pharmaceutically acceptable salts of β-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, hexamidine isothionate, metronidazole; pentamidine, gentamycin, kanamycin, lineomycin, methacycline, methenamine, minocycline, neomycin, netilmycin, paromomycin, streptomycin, tobramycin, miconazole, and amanfadine.

Other drug moieties of use in practicing the present invention include antineoplastic drugs (e.g., antiandrogens (e.g., leuprolide or flutamide), cytocidal agents (e.g., adriamycin, doxorubicin, taxol, cyclophosphamide, busulfan, cisplatin, a-2-interferon) anti-estrogens (e.g., tamoxifen), antimetabolites (e.g., fluorouracil, methotrexate, mercaptopurine, thioguanine).

The recognition moiety can also comprise hormones (e.g., medroxyprogesterone, estradiol, leuprolide, megestrol, octreotide or somatostatin); muscle relaxant drugs (e.g., cinnamedrine, cyclobenzaprine, flavoxate, orphenadrine, papaverine, mebeverine, idaverine, ritodrine, dephenoxylate, dantrolene and azumolen); antispasmodic drugs; boneactive drugs (e.g., diphosphonate and phosphonoalkylphosphinate drug compounds); endocrine modulating drugs (e.g., contraceptives (e.g., ethinodiol, ethinyl estradiol, norethindrone, mestranol, desogestrel, medroxyprogesterone), modulators of diabetes (e.g., glyburide or chlorpropamide), anabolics, such as testolactone or stanozolol, androgens (e.g., methyltestosterone, testosterone or fluoxymesterone), antidiuretics (e.g., desmopressin) and calcitonins).

Also of use in the present invention are estrogens (e.g., diethylstilbesterol), glucocorticoids (e.g., triamcinolone, betamethasone, etc.) and progenstogens, such as norethindrone, ethynodiol, norethindrone, levonorgestrel; thyroid agents (e.g., liothyronine or levothyroxine) or anti-thyroid agents (e.g., methimazole); antihyperprolactinemic drugs (e.g., cabergoline); hormone suppressors (e.g., danazol or goserelin), oxytocics (e.g., methylergonovine or oxytocin) and prostaglandins, such as mioprostol, alprostadil or dinoprostone, can also be employed.

Other useful recognition moieties include immunomodulating drugs (e.g., antihistamines, mast cell stabilizers, such as lodoxamide and/or cromolyn, steroids (e.g., triamcinolone, beclomethazone, cortisone, dexamethasone, prednisolone, methylprednisolone, beclomethasone, or clobetasol), histamine $H_2$ antagonists (e.g., famotidine, cimetidine, ranitidine), immunosuppressants (e.g., azathioprine, cyclosporin), etc. Groups with anti-inflammatory activity, such as sulindac, etodolac, ketoprofen and ketorolac, are also of use. Other drugs of use in conjunction with the present invention will be apparent to those of skill in the art.

When the recognition moiety is a chelating agent, crown ether or cyclodextrin, host-guest chemistry will dominate the interaction between the recognition moiety and the analyte. The use of host-guest chemistry allows a great degree of recognition-moiety-analyte specificity to be engineered into a device of the invention. The use of these compounds to bind to specific compounds is well known to those of skill in the art. See, for example, Pitt et al. "The Design of Chelating Agents for the Treatment of Iron Overload," In, INORGANIC CHEMISTRY IN BIOLOGY AND MEDICINE; Martell, A. E., Ed.; American Chemical Society, Washington, D.C., 1980, pp. 279-312; Lindoy, L. F., THE CHEMISTRY OF MACROCYCLIC LIGAND COMPLEXES; Cambridge University Press, Cambridge, 1989; Dugas, H., BIOORGANIC CHEMISTRY; Springer-Verlag, New York, 1989, and references contained therein.

Additionally, a manifold of routes allowing the attachment of chelating agents, crown ethers and cyclodextrins to other molecules is available to those of skill in the art. See, for example, Meares et al., "Properties of In Vivo Chelate-Tagged Proteins and Polypeptides." In, MODIFICATION OF PROTEINS: FOOD, NUTRITIONAL, AND PHARMACOLOGICAL ASPECTS;" Feeney, R. E., Whitaker, 1.R., Eds., American Chemical Society, Washington, D.C., 1982, pp. 370-387; Kasina et al. *Bioconjugate Chem.* 9:108-117 (1998); Song et al., *Bioconjugate Chem.* 8:249-255 (1997).

In a presently preferred embodiment, the recognition moiety is a polyaminocarboxylate chelating agent such as ethylenediaminetetraacetic acid (EDTA) or diethylenetriaminepentaacetic acid (DTPA). These recognition moieties can be attached to any amine-terminated component of a SAM or a spacer arm, for example, by utilizing the commercially available dianhydride (Aldrich Chemical Co., Milwaukee, Wis.).

In still further preferred embodiments, the recognition moiety is a biomolecule such as a protein, nucleic acid, peptide or an antibody. Biomolecules useful in practicing the present invention can be derived from any source. The biomolecules can be isolated from natural sources or can be produced by synthetic methods. Proteins can be natural proteins or mutated proteins. Mutations can be effected by chemical mutagenesis, site-directed mutagenesis or other means of inducing mutations known to those of skill in the art. Proteins useful in practicing the instant invention include, for example, enzymes, antigens, antibodies and receptors. Antibodies can be either polyclonal or monoclonal. Peptides and nucleic acids can be isolated from natural sources or can be wholly or partially synthetic in origin.

In those embodiments wherein the recognition moiety is a protein or antibody, the protein can be tethered to a SAM component or a spacer arm by any reactive peptide residue available on the surface of the protein. In preferred embodiments, the reactive groups are amines or carboxylates. In particularly preferred embodiments, the reactive groups are the e-amine groups of lysine residues. Furthermore, these molecules can be adsorbed onto the surface of the substrate or SAM by non-specific interactions (e.g., chemisorption, physisorption).

Recognition moieties that are antibodies can be used to recognize analytes that are proteins, peptides, nucleic acids, saccharides or small molecules such as drugs, herbicides, pesticides, industrial chemicals and agents of war. Methods of raising antibodies for specific molecules are well-known to those of skill in the art. See, U.S. Pat. Nos. 5,147,786; 5,334,528; 5,686,237; 5,573,922; each of which is incorporated herein by reference. Methods for attaching antibodies to surfaces are also art-known (See, Delamarche et al. *Langmuir* 12:1944-1946 (1996)).

Peptides and nucleic acids can be attached to a SAM component or spacer arm. Both naturally-derived and synthetic peptides and nucleic acids are of use in conjunction with the present invention. These molecules can be attached to a SAM component or spacer arm by any available reactive group. For example, peptides can be attached through an amine, carboxyl, sulfhydryl, or hydroxyl group. Such a group can reside at a peptide terminus or at a site internal to the peptide chain. Nucleic acids can be attached through a reactive group on a base (e.g., exocyclic amine) or an available hydroxyl group on a sugar moiety (e.g., 3'- or 5'-hydroxyl). The peptide and nucleic acid chains can be further derivatized at one or more sites to allow for the attachment of appropriate reactive groups onto the chain (See, Chrisey et al. *Nucleic Acids Res.* 24:3031-3039 (1996)).

When the peptide or nucleic acid is a fully or partially synthetic molecule, a reactive group or masked reactive group can be incorporated during the process of the synthesis. Many derivatized monomers appropriate for reactive group incorporation in both peptides and nucleic acids are know to those of skill in the art (See, for example, THE PEPTIDES: ANALYSIS, SYNTHESIS, BIOLOGY, Vol. 2: "Special Methods in Peptide Synthesis," Gross, E. and Melenhofer, J., Eds., Academic Press, New York (1980)). Many useful monomers are commercially available (Bachem, Sigma, etc.). This masked group can then be unmasked following the synthesis, at which time it becomes available for reaction with a SAM component or a spacer arm.

In other preferred embodiments, the peptide is attached directly to the substrate (See, Frey et al. *Anal. Chem.* 68:3187-3193 (1996)). In a particularly preferred embodiment, the peptide is attached to a gold substrate through a sulfhydryl group on a cysteine residue. In another preferred embodiment, the peptide is attached through a thiol to a spacer arm which terminates in, for example, an iodoacetamide, chloroacetamide, benzyl iodide, benzyl bromide, alkyl iodide or alkyl bromide. Similar immobilization techniques are known to those of skill in the art (See, for example, Zull et al. *J. Ind Microbiol.* 13:137-143 (1994)).

In another preferred embodiment, the recognition moiety forms an inclusion complex with the analyte of interest. In a particularly preferred embodiment, the recognition moiety is a cyclodextrin or modified cyclodextrin. Cyclodextrins are a group of cyclic oligosaccharides produced by numerous microorganisms. Cyclodextrins have a ring structure that has a basket-like shape. This shape allows cyclodextrins to include many kinds of molecules into their internal cavity (See, for example, Szejtli, J., CYCLODEXTRINS AND THEIR INCLUSION COMPLEXES; Akademiai Klado, Budapest, 1982; and Bender et al., CYCLODEXTRIN CHEMISTRY, Springer-Verlag, Berlin, 1978).

Cyclodextrins are able to form inclusion complexes with an array of organic molecules including, for example, drugs, pesticides, herbicides and agents of war (See, Tenjarla et al., *J. Pharm. Sci.* 87:425-429 (1998); Zughul et al., *Pharm. Dev. Technol.* 3:43-53 (1998); and Albers et al., *Crit. Rev. Ther. Drug Carrier Syst.* 12:311-337 (1995)). Importantly, cyclodextrins are able to discriminate between enantiomers of compounds in their inclusion complexes. Thus, in one preferred embodiment, the invention provides for the detection of a particular enantiomer in a mixture of enantiomers (See, Koppenhoefer et al. *J. Chromatogr. A* 793:153-164 (1998)).

The cyclodextrin recognition moiety can be attached to a SAM component, through a spacer arm or directly to the substrate (See, Yamamoto et al., *J. Phys. Chem. B* 101:6855-6860 (1997)). Methods to attach cyclodextrins to other molecules are well known to those of skill in the chromatographic and pharmaceutical arts (See, Sreenivasan, *Appl. Polym. Sci.* 60:2245-2249 (1996)).

IV. Mesogenic Layer

Any compound or mixture of compounds that forms a mesogenic layer can be used in conjunction with the present invention. The mesogens can form thermotropic or lyotropic liquid crystals. The mesogenic layer can be either continuous or it can be patterned.

Both the thermotropic and lyotropic liquid crystals can exist in a number of forms including nematic, chiral nematic, smectic, polar smectic, chiral smectic, frustrated phases and discotic phases.

TABLE 1

Molecular structure of mesogens suitable for use in Liquid Crystal Assay Devices

| Mesogen | Structure |
|---|---|
| Anisaldazine | 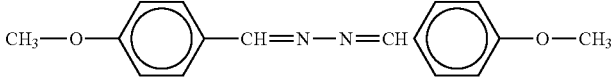 |
| NCB | 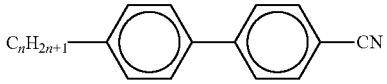 |
| CBOOA | 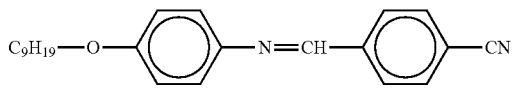 |
| Comp A | 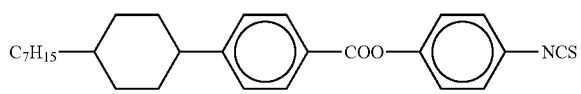 |
| Comp B | 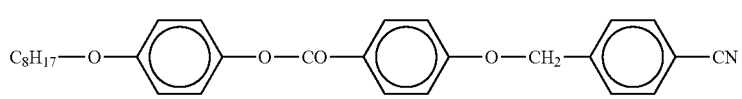 |
| DB$_7$NO$_2$ | 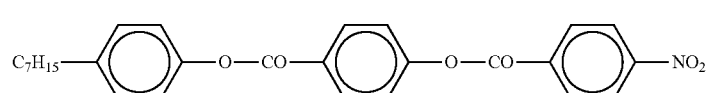 |
| DOBAMBC | 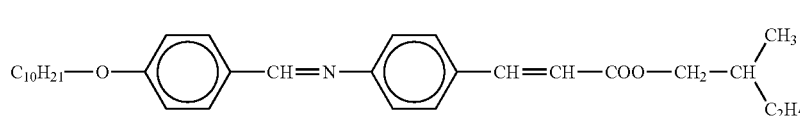 |
| nOm<br>n = 1, m = 4: MBBA<br>n = 2, m = 4: EBBA | 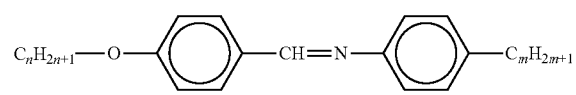 |
| nOBA<br>n = 8: OOBA<br>n = 9: NOBA | 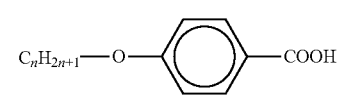 |
| nmOBC | 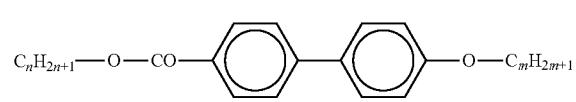 |
| nOCB | 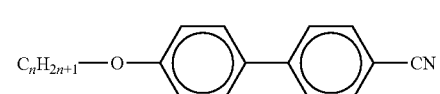 |

TABLE 1-continued

Molecular structure of mesogens suitable for use in Liquid Crystal Assay Devices

| Mesogen | Structure |
|---|---|
| nOSI | $C_nH_{2n+1}$—O—⟨⟩—⟨⟩—COO—⟨⟩—$CH_2$—CH($CH_3$)($C_2H_5$) |
| 98P | $C_3H_7$—$[CH_2(CH_3)]_5$—O—⟨⟩—⟨N=N⟩—$C_8H_{17}$ |
| PAA | $CH_3$—O—⟨⟩—N=N(→O)—⟨⟩—O—$CH_3$ |
| PYP906 | $C_9H_{19}$—⟨N=N⟩—⟨⟩—O—$C_6H_{13}$ |
| $\overline{n}Sm$ | $C_nH_{2n+1}$—O—⟨⟩—CO—S—⟨⟩—$C_mH_{2m+1}$ |

Presently preferred mesogens are displayed in Table 1. In a particularly preferred embodiment, the mesogen is a member selected from the group consisting of 4-cyano-4'-pentylbiphenyl, N-(4methoxybenzylidene)-4-butlyaniline and combinations thereof.

The mesogenic layer can be a substantially pure compound, or it can contain other compounds that enhance or alter characteristics of the mesogen. Thus, in one preferred embodiment, the mesogenic layer further comprises a second compound, for example and alkane, which expands the temperature range over which the nematic and isotropic phases exist. Use of devices having mesogenic layers of this composition allows for detection of the analyte recognition moiety interaction over a greater temperature range.

In some preferred embodiments, the mesogenic layer further comprises a dichroic dye or fluorescent compound. Examples of dichroic dyes and fluorescent compounds useful in the present invention include, but are not limited to, azobenzene, BTBP, polyazocompunds, anthraquinone, perylene dyes, and the like. In particularly preferred embodiments, a dichroic dye of fluorescent compound is selected that complements the orientation dependence of the liquid crystal so that polarized light is not required to read the assay. In some preferred embodiments, if the absorbance of the liquid crystal is in the visible range, then changes in orientation can be observed using ambient light without crossed polars. In other preferred embodiments, the dichroic dye or fluorescent compound is used in combination with a fluorimeter and the changes in fluorescence are used to detect changes in orientation of the liquid crystal.

In another preferred embodiment, the analyte first interacts with the recognition moiety and the mesogenic layer is introduced in its isotropic phase. The mesogenic layer is subsequently cooled to form the liquid crystalline phase. The presence of the analyte within regions of the mesogenic layer will disturb the equilibrium between the nematic and isotropic phases leading to different rates and magnitudes of nucleation at those sites. The differences between the nematic and isotropic regions are clearly detectable.

V. Patterned Liquid Crystals

One approach to the patterning of the mesogenic layer on flat and curved surfaces is based on the use of patterned SAMs of molecules to direct both the polar (away from the surface) and azimuthal (in the plane of the surface) orientations of the mesogenic layer. This method is simple and flexible, and any of the recently established procedures for patterning SAMs on surfaces (for example, microcontact printing or photo-patterning) (Talov et al., J. Am. Chem. Soc. 115: 5305 (1993); Kumar et al., Acc. Chem. Res. 28: 219 (1995), and references therein; Xia et al., J. Am. Chem. Soc. 117: 3274 (1995), and references therein can be used; Jackman et al., Science 269: 664 (1995)). Using any of these methods, SAMs which pattern liquid crystals can be easily extended to sizes ranging from hundreds of nanometers (Xia et al., J. Am. Chem. Soc. 117: 3274 (1995), and references therein) to millimeters and permit both planar (parallel to the surface) and homeotropic (perpendicular to the surface) orientation of mesogenic layers; methods based on the rubbing of polymer films mainly provide manipulation of the in-plane alignment of mesogenic layers and cannot homeotropically align mesogenic layers. One class of useful SAMs has surface energies (~19 mJ/m$^2$) about half those of films of polyimides used for alignment of liquid crystals; low-energy surfaces are less prone to contamination by molecular adsorbates and dust particles than are high-energy ones. Because SAMs can also be patterned on non-planar surfaces (Jackman et al., Science 269: 664 (1995)), patterned mesogenic structures formed with SAMs can be replicated on curved surfaces.

The capacity to pattern mesogenic layer orientations on nonplanar surfaces provides procedures for the fabrication of tunable hybrid diffractive-refractive devices. For example, devices based on combinations of diffractive and refractive optical processes permit aplanatic or chromatic correction in lenses, spectral dispersion, imaging from a single optical element, and other manipulations of light (Resler et al., Opt. Lett. 21, 689 (1996); S. M. Ebstein, ibid., p. 1454; M. B. Stem, Microelectron. Eng. 32, 369 (1996): Goto et al., Jpn. J. Appl. Phys. 31, 1586 (1992); Magiera et al., Soc. Photo-Opt. Instrum. Eng., 2774, 204 (1996)). The capability to pattern mesogenic layers on curved surfaces also provides routes for the fabrication of displays with wide viewing angles.

In a presently preferred embodiment, the tunable hybrid device permits the manipulation of light. In a further preferred embodiment, the device is a refractive-diffractive device. In a still further preferred embodiment, the device permits imaging from a single optical element. In yet another preferred embodiment, the device permits aplanatic or chromatic correction in lenses. In still another preferred embodiment, the device allows for spectral dispersion.

In another presently preferred embodiment, the SAM is layered on a material suitable for use as an electrode. In a preferred embodiment, the material is a metal film. In a further preferred embodiment, the metal film is a gold film.

The patterned mesogenic layers of the instant invention can be tuned by the use of electric fields. In a preferred embodiment, the electric field is used to reversibly orient the mesogenic layer. In a still further preferred embodiment, the electric field is applied either perpendicular to, or in the plane of, the surface of the mesogenic layer. In another preferred embodiment, the oriented mesogenic layer modulates the intensity of light diffracted from the layer.

The discussion above, concerning SAM components, SAM components with reactive groups and SAM components bearing recognition moieties is equally applicable in the context of this aspect of the invention. Thus, the constituents of the SAM can be chosen from any of a wide variety of appropriate molecules. In a presently preferred embodiment, the SAM comprises mixtures of $R^{21}CH_2(CH_2)_{14}SH$ and $R^{31}CH_2(CH_2)_{15}SH$, where $R^{21}$ and $R^{31}$ are independently members elected from the group consisting of hydrogen, reactive groups and recognition groups, as discussed above.

VI. Analytes

It is contemplated that the devices and methods of the present invention can be used to detect any analyte, or class of analytes, which interact with a recognition moiety in a manner that perturbs the mesogenic layer in a detectable manner. This statement does not appear to include non-specific interactions. The interaction between the analyte and recognition moiety can be any physicochemical interaction, including covalent bonding, ionic bonding, hydrogen bonding, van der Waals interactions, repulsive electronic interactions, attractive electronic interactions and hydrophobic/hydrophilic interactions.

In a preferred embodiment, the interaction is an ionic interaction. In this embodiment, an acid, base, metal ion or metal ion-binding ligand is the analyte. In a still further preferred embodiment, the interaction is a hydrogen bonding interaction. In a particularly preferred embodiment, the hybridization of an immobilized nucleic acid to a nucleic acid having a complementary sequence is detected. In another preferred embodiment, the interaction is between an enzyme or receptor and a small molecule that binds thereto.

In another embodiment, the analyte competes for the recognition moiety with another agent, which has been bound to the recognition moiety prior to introducing the analyte of interest. In this embodiment, it is the process or result of the analyte displacing the pre-bound agent, which causes the detectable perturbation in the mesogenic layer.

Suitable combinations of recognition moieties and analytes will be apparent to those of skill in the art.

In presently preferred embodiments, the analyte is a member selected from the group consisting of acids, bases, organic ions, inorganic ions, pharmaceuticals, herbicides, pesticides, chemical warfare agents, noxious gases, biomolecules (e.g., polypeptides, carbohydrates, and polynucleotides) and microorganisms (e.g., viruses, bacteria, prions, mycoplasmas, etc.). Importantly, each of these agents can be detected as a vapor or in a liquid solution. These agents can be present as components in mixtures of structurally unrelated compounds, racemic mixtures of stereoisomers, non-racemic mixtures of stereoisomers, mixtures of diastereomers, mixtures of positional isomers or as pure compounds. Within the scope of the invention is a device and a method to detect a particular analyte of interest without interference from other substances within a mixture.

Both organic and inorganic acids can be detected using the device and method of the present invention. In a preferred embodiment, the recognition moiety comprises a group that is protonated by the acid. The result of this protonation is a detectable perturbation in the configuration of the mesogenic layer. While not wishing to be bound by any particular theory of operation, the inventors currently believe that this perturbation can be achieved by a change in the size or conformation of the recognition moiety on protonation. Alternatively, the protonation may induce repulsion between proximate recognition moieties bearing charges of the same sign. Further, the protonation can induce an overall positive charge across the SAM, which perturbs the electronic distribution of the molecules in the mesogenic layer. This perturbation can be due to an electronic redistribution in the mesogenic molecules or can be due to repulsive or attractive interaction between a charged mesogen and a similarly, or oppositely, charged SAM.

In another preferred embodiment, the invention provides a device and a method for detecting bases. The methods for the detection and the mechanisms which allow such detection of bases are substantially similar to those discussed above in the context of acid detection; the notable exception being that the base will preferably deprotonate a group on a SAM component, spacer arm or substrate.

Organic ions that are substantially non-acidic and non-basic (e.g., quaternary alkylammonium salts) can be detected by a recognition moiety. For example, a recognition moiety with ion exchange properties is useful in the present invention. A specific example is the exchange of a cation such as dodecyltrimethylammonium cation for a metal ion such as sodium, using a SAM presenting. Recognition moieties that form inclusion complexes with organic cations are also of use. For example, crown ethers and cryptands can be used to form inclusion complexes with organic ions such as quaternary ammonium canons.

Inorganic ions such as metal ions and complex ions (e.g., $SO_4$, $PO_4$) can also be detected using the device and method of the invention. Metal ions can be detected, for example, by their complexation or chelanon by agents bound to a SAM component, spacer arm or the substrate. In this embodiment, the recognition moiety can be a simple monovalent moiety (e.g., carboxylate, amine, thiol) or can be a more structurally complex agent (e.g., ethylenediaminepentaacetic acid, crown ethers, aza crowns, thia crowns). The methods of detection and the mechanisms allowing such detection are substantially similar to those discussed in the context of acid detection.

Complex inorganic ions can be detected by their ability to compete with ligands for bound metal ions in ligand-metal complexes. When a ligand bound to a SAM component, a spacer arm or a substrate forms a metal-complex having a thermodynamic stability constant which is less than that of the complex between the metal and the complex ion, the complex ion will cause the dissociation of the metal ion from the immobilized ligand. The dissociation of the metal ion will perturb the mesogenic layer in a detectable manner. Methods of determining stability constants for compounds formed between metal ions and ligands are well known to those of skill in the art. Using these stability constants, devices that are specific for particular ions can be manufactured. See, Martell, A. E., Motekaitis, R. J., DETERMINATION AND USE OF STABILITY CONSTANTS, 2d Ed., VCH Publishers, New York 1992.

Small molecules such as pesticides, herbicides, agents of war, and the like can be detected by the use of a number of different recognition moiety motifs. Acidic or basic components can be detected as described above. An agent's metal binding capability can also be used to advantage, as described above for complex ions. Additionally, if these agents bind to an identified biological structure (e.g., a receptor), the receptor can be immobilized on the substrate, a SAM component or a spacer arm. Techniques are also available in the art for raising antibodies that are highly specific for a particular small molecule. Thus, it is within the scope of the present invention to make use of antibodies against small molecules for detection of those molecules.

In a preferred embodiment, the affinity of an analyte for a particular metal ion is exploited by having a SAM component, spacer arm or substrate labeled with an immobilized metal ion. The metal ion generally must have available at least one empty coordination site to which the analyte can bind. Alternatively, at least one bond between the metal and the metal-immobilizing agent must be sufficiently labile in the presence of the analyte to allow the displacement of at least one bond of the immobilizing reagent by the analyte.

In a preferred embodiment, the agent detected by binding to an immobilized metal ion is an organophosphorous compound such as an insecticide or an agent of war (e.g., VX, O-ethyl-S-(2-diisopropylaminoethyl) methylthiophosphonate). Exemplary compounds which exhibit affinity for organophosphorous agents include, but are not limited to, $Cu^{+2}$-diamine, triethylentetraamine-$Cu^{+2}$-chloride, tetraethylenediamine-$Cu^{+2}$-chloride and 2,2' bipyridine-$Cu^{+2}$-chloride (U.S. Pat. No. 4,549,427, incorporated herein by reference).

In another preferred embodiment, antibodies to the particular agents are immobilized on the substrate, a SAM component or a spacer arm. Techniques for raising antibodies to herbicides, pesticides and agents of war are known to those of skill in the art. See, Harlow, Lane, MONOCLONAL ANTIBODIES: A LABORATORY MANUAL, Cold Springs Harbor Laboratory, Long Island, N.Y., 1988.

In a preferred embodiment, the herbicides are preferably members of the group consisting of triazines, haloacetanilides, carbamates, toluidines, areas, plant growth hormones and diphenyl ethers. Included within these broad generic groupings are commercially available herbicides such as phenoxyl alkanoic acids, bipyridiniums, benzonitriles, dinitroanilines, acid amides, carbamates, thiocarbamates, heterocyclic nitrogen compounds including triazines, pyridines, pyridazinones, sulfonylureas, imazoles, substituted areas, halogenated aliphatic carboxylic acids, inorganics, organometallics and derivatives of biologically important amino acids.

In the embodiments discussed above, the preferred agent of war is a member of the group consisting of mustard and related vesicants including the agents known as HD, Q, T, HN1, HN2, HN3, nerve agents, particularly the organic esters of substituted phosphoric acid including tabun, sarin, isopropyl methylphosphonofluoridate, soman pinacolyl methylphosphonofluoridate. Other detectable analytes include incapacitants such as BZ, 3-quinuclidinyl benzilate and irritants such as the riot control compound CS.

Pesticides preferred for detection using the present invention include bactericides (e.g., formaldehyde), fumigants (e.g., bromomethane), fungicides (e.g., 2phenylphenol, biphenyl, mercuric oxide, imazalil), acaricides (e.g., abamectin, bifenthrin), insecticides (e.g., imidacloprid, prallethrin, cyphenothrin)

The present invention also provides a device and a method for detecting noxious gases such as CO, $CO_2$, $SO_3$, $H_2SO_4$, $SO_2$, NO, $NO_2$, $N_2O_4$ and the like. In a preferred embodiment, the SAM, the substrate or a spacer arm includes at least one compound capable of detecting the gas. Useful compounds include, but are not limited to, palladium compounds selected from the group consisting of palladium sulfate, palladium sulfite, palladium pyrosulfite, palladium chloride, palladium bromide, palladium iodide, palladium perchlorate, palladium complexes with organic complexing reagents and mixtures thereof.

Other compounds of use in practicing this embodiment of the present invention include, molybdenum compounds such as silicomolybdic acid, salts of silicomolybdic acid, molybdenum trioxide, heteropolyacids of molybdenum containing vanadium, copper or tungsten, ammonium molybdate, alkali metal or alkaline earth salts of molybdate anion, heteropolymolybdates and mixtures thereof.

Still further useful gas detecting compounds include, copper salts and copper complexes with an available coordination site. Alpha-cyclodextrin, betacyclodextrin, modified alpha- and beta-cyclodextrins, gamma-cyclodextrin and mixtures thereof are of use in practicing the present invention (U.S. Pat. Nos. 5,618,493, and 5,071,526, each of which is incorporated herein by reference).

In another preferred gas detecting embodiment, the substrate, SAM component or spacer arm is derivatized with a compound selected from the group consisting of amorphous hemoglobin, crystalline hemoglobin, amorphous heme, crystalline heme and mixtures thereof. The heme serves as a recognition moiety that is reactive towards the gas (U.S. Pat. No. 3,693,327, incorporated herein by reference).

When the analyte is a biomolecule, any recognition moiety that interacts with the biomolecule is useful in practicing the present invention. Thus, when the analyte is a nucleic acid, in one embodiment, the recognition moiety is a nucleic acid having a sequence that is at least partially complementary to the recognition moiety sequence. When the recognition moiety is a peptide, an antibody specific for that peptide can be used as the analyte. In another preferred embodiment, a protein, other than an antibody (e.g., enzyme, receptor) is the analyte.

In a presently preferred embodiment, the recognition moiety interacts with biotin and is avidin or an anti-biotin antibody. Other recognition moieties of use when the analyte is a biomolecule will be apparent to those of skill in the art.

In still further preferred embodiments, microorganisms, including pathogens are detected. In some embodiments, the recognition moiety used to detect microorganisms is an antibody directed to the microorganism. In other embodiments, ligands are incorporated to detect a variety of pathogenic organisms including, but not limited to, sialic acid to detect HIV (Wies et al., Nature 333: 426 [1988]), influenza (White et al., Cell 56: 725 [1989]), *Chlamydia* (Infect. Imm.

57: 2378 [1989]), *Neisseria meningitidis, Streptococcus suis, Salmonella*, mumps, newcastle, and various viruses, including reovirus, Sendai virus, and myxovirus; and 9-OAC sialic acid to detect coronavirus, encephalomyelitis virus, and rotavirus; non-sialic acid glycoproteins to detect cytomegalovirus (Virology 176: 337 [1990]) and measles virus (Virology 172: 386 [1989]); CD4 (Khatzman et al., Nature 312: 763 [1985]), vasoactive intestinal peptide (Sacerdote et al., J. of Neuroscience Research 18: 102 [1987]), and peptide T (Ruff et al., FEBS Letters 211: 17 [1987]) to detect HIV; epidermal growth factor to detect vaccinia (Epstein et al., Nature 318: 663 [1985]); acetylcholine receptor to detect rabies (Lentz et al., Science 215: 182 [1982]); Cd3 complement receptor to detect Epstein-Barr virus (Carel et al., J. Biol. Chem. 265: 12293 [1990]); -adrenergic receptor to detect reovirus (Co et al., Proc. Natl. Acad. Sci. 82: 1494 [1985]); ICAM-1 (Marlin et al., Nature 344: 70 [1990]), N-CAM, and myelin-associated glycoprotein MAb (Shephey et al., Proc. Natl. Acad. Sci. 85: 7743 [1988]) to detect rhinovirus; polio virus receptor to detect polio virus (Mendelsohn et al., Cell 56: 855 [1989]); fibroblast growth factor receptor to detect herpes virus (Kaner et al., Science 248: 1410 [1990]); oligomannose to detect Escherichia coli; ganglioside G to detect *Neisseria meningitidis*; and antibodies to detect a broad variety of pathogens (e.g., *Neisseria gonorrhoeae, V. vulnificus, V. parahaemolyticus, V. cholerae*, and *V. alginolyticus*).

VII. Compound Libraries

The synthesis and screening of chemical libraries to identify compounds that have novel pharmacological and material science properties is a common practice. Libraries that have been synthesized include, for example, collections of oligonucleotides, oligopeptides, and small or large molecular weight organic or inorganic molecules. See WO 97/35198, WO 96/40732, and Gallop et al., *J. Med. Chem.* 37:1233-51 (1994).

Thus, in some embodiments, the invention provides a device for synthesizing and screening a library of compounds, comprising:

(1) a synthesis component, comprising:
  (a) a first substrate having a surface;
  (b) a self-assembled monolayer on the surface, said monolayer comprising a reactive functionality; and
(2) an analysis component, comprising:
  (a) a second substrate having a surface; and
  (b) a mesogenic layer between said surface of said first substrate and said surface of said second substrate.

In a preferred embodiment, the second substrate has a self-assembled monolayer attached thereto. In yet another preferred embodiment, the second substrate is permeable to liquids, vapors, gases and combinations thereof. The permeable substrate allows analytes to come into contact with the self-assembled monolayer(s) and the mesogenic layer, while maintaining the overall integrity of the optical cell.

The discussion above concerning substrates, organic layers and mesogenic layers is applicable to each of the embodiments of this aspect of the invention. In a presently preferred embodiment, the substrate comprises a metal film. In a further preferred embodiment, the metal film is a member selected from the group consisting of gold, nickel, platinum, silver, palladium and copper. In a still further preferred embodiment, the metal film is obliquely deposited.

The organic layer can be constructed of any organic substance which associates with the substrate, preferably, the organic layer constituents are moieties selected from the group consisting of alkanethiols, functionalized alkanethiols and combinations thereof. In a further preferred embodiment, at least one component of the organic layer is a moiety which is a member selected from the group consisting of $R^{21}CH_2(CH_2)_{14}SH$ and $R^{31}CH_2(CH_2)_{15}SH$, wherein $R^{21}$ and $R^{31}$ are independently members selected from the group consisting of hydrogen, reactive groups and recognition moieties.

The discussion above concerning reactive groups is equally applicable to this aspect of the invention. In certain preferred embodiments, $R^{21}$ and $R^{31}$ are independently members selected from the group consisting of hydrogen, amine, carboxylic acid, carboxylic acid derivatives, alcohols, thiols, alkenes and combinations thereof.

The SAM can be patterned by any of the above-discussed methods for producing patterned substrates and organic layers. The discussion above concerning the patterning of substrates and the construction of organic layers from a mixture of components having different properties is generally applicable to this embodiment of the invention. In a presently preferred embodiment, the SAM is patterned by microcontact printing. In a further preferred embodiment, the microcontact printing utilizes a component that is distinct from the components of the self-assembled monolayer.

The mesogenic layer can comprise one or more mesogenic compounds. The discussion above concerning the nature of the mesogenic layer is generally applicable to this embodiment of the invention. In a presently preferred embodiment, the mesogenic layer comprises a mesogen which is a member selected from the group consisting of 4-cyano-4'-pentylbiphenyl, N-(4-methoxybenzylidene)-4-butylanailine and combinations thereof.

In another preferred embodiment, the present invention provides a method for synthesizing and analyzing a combinatorial library of compounds using the above described device. The method comprises, (a) adding a first component of a first compound to a first region of said surface of said first substrate and a first component of a second compound to a second region of said surface of said first substrate;

(b) adding a second component of said first compound to said first region of said surface of said first substrate and adding a second component of said second compound to said second region on said surface of said first substrate;

(c) reacting said first and second components to form a first product and a second product;

(d) applying said mesogenic layer to said surface of said first substrate;

(e) adding an analyte to said first region and said second region; and (f) detecting said switch in said mesogenic layer from a first orientation to said second orientation, whereby said analyzing is achieved.

The sequential addition of components can be repeated as many times as necessary in order to assemble the desired library of compounds. Additionally, any number of solvents, catalysts and reagents necessary to effect the desired molecular transformations can be added before, concurrently or after the addition of the component.

Virtually any type of compound library can be synthesized using the method of the invention, including peptides, nucleic acids, saccharides, and small and large molecular weight organic and inorganic compounds.

In a presently preferred embodiment, when the synthesis is complete, a second substrate is layered on top of the mesogenic layer. In a further preferred embodiment, the second substrate has an attached second self-assembled monolayer that contacts the mesogenic layer. The discussion above concerning the permutations available when two substrates are utilized is generally applicable to this embodiment. In a still further preferred embodiment, the second substrate is a permeable substrate. In yet another preferred embodiment, the second substrate is patterned similar to the first substrate.

In a presently preferred embodiment, the libraries synthesized comprise more than 10 unique compounds, preferably more than 100 unique compounds and more preferably more than 1000 unique compounds.

In still further embodiments, the present invention also provides a library of compounds synthesized on a self-assembled monolayer. The discussion above concerning libraries, SAMs, functionalized SAM components, mesogenic layers, and the like is generally applicable to this aspect of the invention.

VIII. The Device

The device of the present invention can be of any configuration that allows for the contact of a mesogenic layer with an organic layer or inorganic layer (e.g., metal, metal salt or metal oxide). The only limitations on size and shape are those that arise from the situation in which the device is used or the purpose for which it is intended. The device can be planar or non-planar. Thus, it is within the scope of the present invention to use any number of polarizers, lenses, filters lights, and the like to practice the present invention.

Although many changes in the mesogenic layer can be detected by visual observation under ambient light, any means for detecting the change in the mesogenic layer can be incorporated into, or used in conjunction with, the device. Thus, it is within the scope of the present invention to use lights, microscopes, spectrometry, electrical techniques and the like to aid in the detection of a change in the mesogenic layer.

In those embodiments utilizing light in the visible region of the spectrum, the light can be used to simply illuminate details of the mesogenic layer. Alternatively, the light can be passed through the mesogenic layer and the amount of light transmitted, absorbed or reflected can be measured. The device can utilize a backlighting device such as that described in U.S. Pat. No. 5,739,879, incorporated herein by reference. Light in the ultraviolet and infrared regions is also of use in the present invention.

Thus, in another aspect, the invention provides a method for varying the optical texture of a mesogenic layer comprising a haloorganosulfur. The haloorganosulfur has a halogen content. The optical texture of the mesogenic layer is controlled by selecting the halogen content of the haloorganosulfur.

The present invention contemplates the use of plate readers to detect changes in the orientation of mesogens upon binding of an analyte. The plate readers may be used in conjunction with the LC assay devices described herein and also with the lyotropic LC assays described in U.S. Pat. No. 6,171,802, incorporated herein by reference. In particular, the present invention includes methods and processes for the quantification of light transmission through films of liquid crystals based on quantification of transmitted or reflected light.

The present invention is not limited to any particular mechanism of action. Indeed, an understanding of the mechanism of action is not required to practice the present invention. Nevertheless, it is contemplated that ordered nanostructured substrates impart order to thin films of liquid crystal placed onto their surface. These ordered films of liquid crystal preserve the plane of polarized light passed through them. If the liquid crystal possesses a well-defined distortion—such as a 90 degree twist distortion—then the liquid crystal will change the polarization of the transmitted light in a well-defined and predictable manner. It is further contemplated that ordered films of liquid crystal differentially absorb (relative to randomly ordered films of liquid crystal) specific wavelengths of light.

In some embodiments of the present invention, the amount of target molecule or molecules bound to a sensing surface of an LC assay device (i.e., a surface decorated with a recognition moiety) increases with the concentration/amount of target molecule present in a sample in contact with a sensing surface. In preferred embodiments, the amount of bound target molecule changes the degree of disorder introduced into a thin film of liquid crystal that is ordered by nature of the underlying nanostructured sensing substrate. In some embodiments, the degree of order present in a thin film of liquid crystal determines the amount of light transmitted through the film when viewed through crossed polars. In other embodiments, the degree of order present in a thin film of liquid crystal determines the amount of light transmitted through the film when viewed using specific wavelengths of light. In still other embodiments, the reflectivity of an interface to a liquid crystal can change with the orientation of the liquid crystal. Therefore, in some embodiments, oblique illumination of the LC assay device is utilized with collection and analysis of reflected light being performed.

Accordingly, the present invention contemplates the use of plate readers to detect light transmission through an LC assay device when viewed through cross polars, the transmission of light through an LC assay device illuminated with a suitable wavelength of light, or reflection of light (i.e., polarized light or non-polarized light of specific wavelengths) from the surface of an LC assay device. In particularly preferred embodiments, plate readers are provided that are designed to be used in conjunction with LC assays. Other embodiments of the present invention provide modified commercially available readers such as ELISA readers and fluorometric readers adapted to read LC assays.

Figure 2:
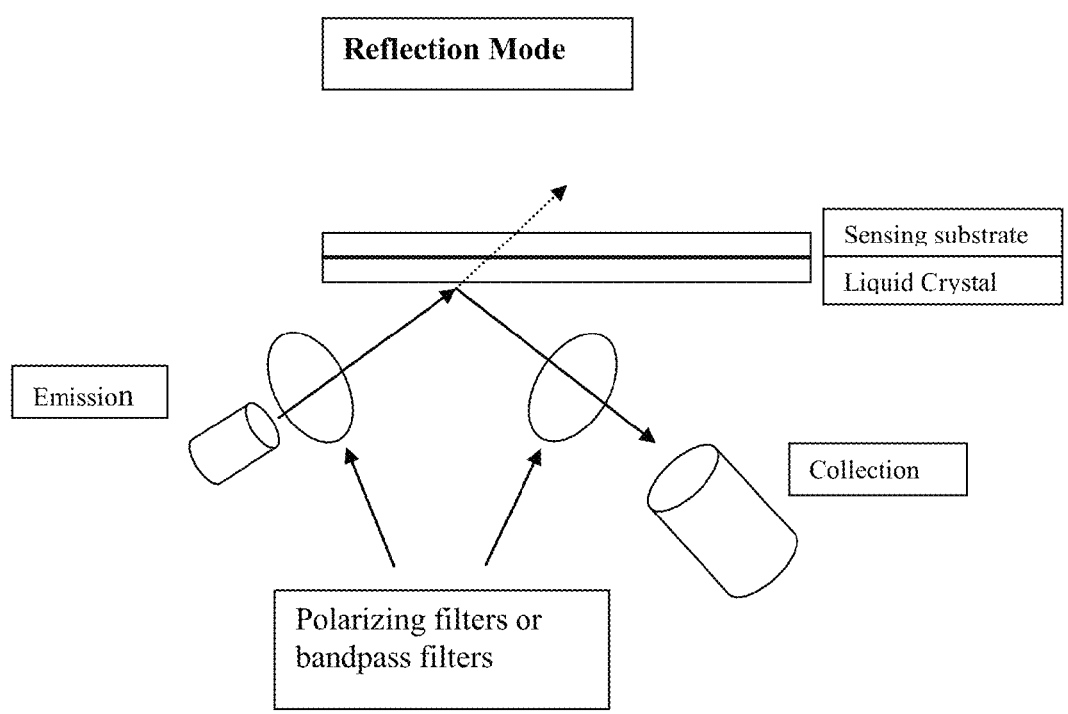
FIG. 2 is schematic depiction of a plate reading device of the present invention.
Figure 3A:
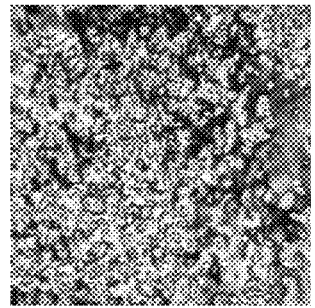
FIGS. 3 A, B, C and D shows disrupted liquid crystal orientation due to non-specific adsorption of BSA. The optical textures shown in FIG. 3B were obtained after rotation of the cell shown in FIG. 3A by 45°.
Figure 3B:
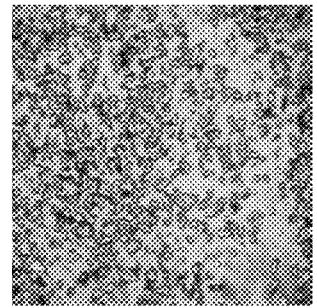
Figure 3C:
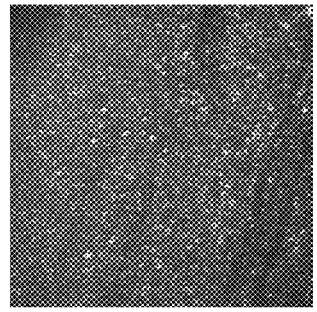
Figure 3D:
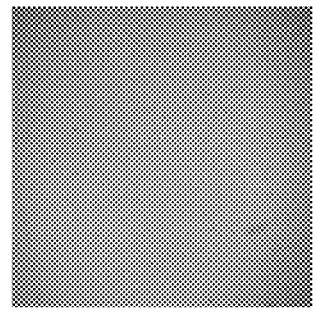
Figure 4A:
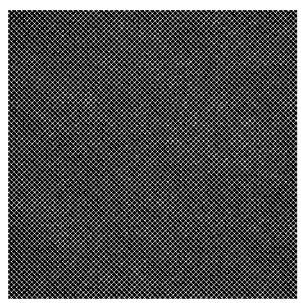
FIGS. 4 A, B, C and D shows uniform, homeotropic liquid crystal orientation in the absence of BSA. The optical appearance shown in FIG. 4B was obtained after rotation of the cell shown in FIG. 4A by 45°.
Figure 4B:
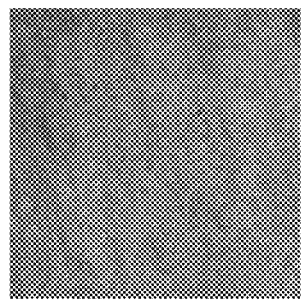
Figure 4C:
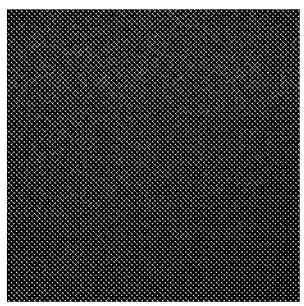
Figure 4D:
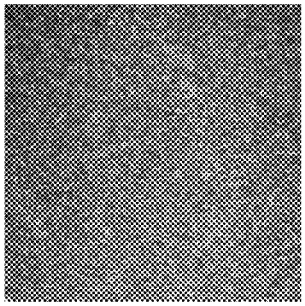
Figure 5A:
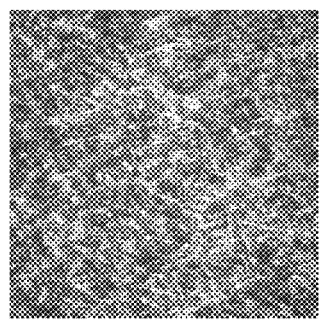
FIGS. 5 A, B, C, and D shows optical textures of 5CB (crossed polarizers) sandwiched between non-stretched Parafilm and OTS-coated glass microscope slides. The optical textures shown in FIG. 5B were obtained after rotation of the cell shown in FIG. 5A by 45°.
Figure 5B:
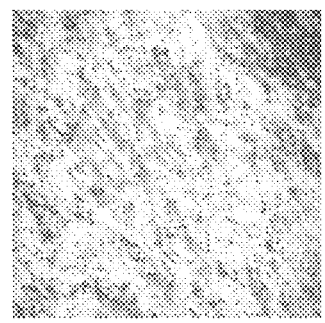
Figure 5C:
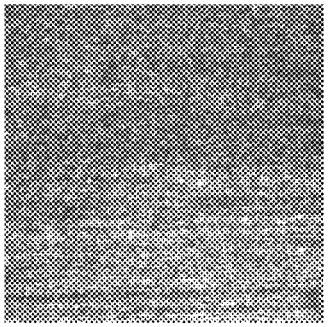
Figure 5D:
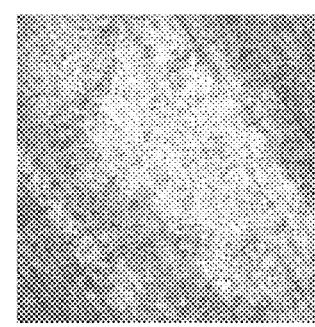

Non-limiting examples of the plate readers of the present invention are provided in FIGS. 1 and 2. In preferred embodiments, two polarizing filters are placed in the optical pathway of the plate reader in a crossed or parallel polar configuration. One filter is placed on the emission side of the light path prior to passing through the sample while a second polarizing filter is placed on the analyzing side of the light path after light has passed through the sample but before it is collected by a sensing devise such as a photodiode or a CCD. An ordered liquid crystal in the LC assay device preserves the plane of polarization and the amount of light reaching the light gathering and sensing device is markedly attenuated when viewed through cross polars or markedly accentuated when viwed through parallel polars. Random organization of the liquid crystal of the LC assay device does not preserve the plane of polarization and the amount of light, passing through crossed polars, reaching the light collecting and sensing device is relatively unaffected. Accordingly, in preferred embodiments, the binding of target molecules by the recognition moieties in an LC assay device introduces disorder into the overlying thin film of LC that increases with the amount of bound target molecule. In other embodiments, specific bandpass filters are placed on the excitation side of the light path before light encounters the sample as well as on the emission side of the light path (after light has passed through or is reflected by the sample but before reaching the light collecting and sensing device (e.g., photodiode or CCD). This configuration is useful for quantifying both reflected and transmitted light The present invention also provides LC assay devices configured for use in the plate reader. In preferred embodiments, the LC assay device is formatted or arrayed according to the dimensions of standard commercially available plates (e.g., 24, 96, 384 and 1536 well plates). In some embodiments, the LC assay device comprises a surface (e.g., a substrate with recognition moieties attached) that is of proper external dimensions to be accurately fit into a given commercial reader. In some embodiments, the substrate contains uniform topography across its surface, while in other embodiments, the substrate contains a gradient of topographies across its surface. The recognition moieties may be arrayed on the substrate surface in any appropriate configuration. For example, in some embodiments, a single binding antibody, polypeptide, or polynucleotide is evenly distributed across the surface. In other embodiments, a single binding antibody, polypeptide, or polynucleotide is distributed across the surface in a gradient. In still other embodiments, a single binding antibody, polypeptide, or polynucleotide is arrayed in discrete spots that are in proper alignment to be read by the commercial reader. In still further embodiments, a variety of different antibodies, polypeptides, or polynucleotides are arrayed in spots that are in proper alignment to read by the commercial reader. In still other embodiments, a variety of different antibodies, polypeptides, or polynucleotides are arrayed in zones along the surface. In the drawing below each zone would contain a different antibody or binding sequence. The plate would be read at predetermined points (e.g., spots corresponding to the location of the wells in a 96 well plate). By designing the zones to the configuration of the plate reader it will be known which "well" readings correspond to each zone. In other embodiments, specifically designed well inserts (to be used with commercially available 24, 96, 384 or 1536 well plates) containing the nanostructured sensing surface will be used in conjunction with commercially available multiwell plates for performing the LC assays.

It will also be recognized that the present invention provides an assay system comprising a plate reading device and an LC assay device, wherein the plate reading device and LC assay device are configured so that light provided from the plate reading device which is passed through or reflected from at least one surface of the LC assay device is detected by a detection unit of the plate reading device. Suitable detecting units include CCDs and photomultiplier tubes.

Commercially available plate readers that may be modified according to the present invention include, but are not limited, to those available from Nalge Nunc International Corporation (Rochester, N.Y.), Greiner America, Inc. (Lake Mary, Fla.), Akers Laboratories Inc., (Thorofare, N.J.), Alpha Diagnostic International, Inc. (San Antonio, Tex.), and Qiagen Inc. (Valencia, Calif.).

X. Quantitation of Analytes

The present invention provides devices and methods for quantitating the amount an analyte in a sample. In some embodiments, the devices of the present invention include electrodes for applying an electrical field across the liquid crystal. It is contemplated that the threshold electrical field (applied voltage) required to detect (e.g., optically or electrically) the onset of reorientation of the liquid crystal will be correlated to the presence of bound analyte. Without being bound to any particular theory, it is believed the presence of the bound analyte will change the strength of anchoring of the liquid crystal and therefore be useful in both detecting a bound analyte, and in particularly preferred embodiments, quantifying the amount of bound analyte.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); μg (micrograms); ng (nanograms); l or L (liters); ml (milliliters); μl (microliters); cm (centimeters); mm (millimeters); μm (micrometers); nm (nanometers); C (degrees Centigrade); U (units), mU (milliunits); min. (minutes); sec. (seconds); % (percent); kb (kilobase); by (base pair); PCR (polymerase chain reaction); BSA (bovine serum albumin).

Example 1

This Example describes the detection of non-specific adsorption of a molecule to a surface. An electron beam evaporator is used to obliquely deposit 30 Angstroms of titanium and then 130 Angstroms of gold onto immobile glass microscope slides. The rate of deposition of the metals is 0.2 Angstroms/sec and the angle of deposition is 50 degrees from the normal. This gold film is immersed into an ethanolic solution of hexadecanethiol to form a hydrophobic monolayer on the surface of the gold film. A droplet of 10 micromolar BSA in PBS is then placed on the surface of the hydrophobic gold film for 20 mins. The droplet is then rinsed from the surface using PBS, then water. The functionalized gold film is then paired with a second gold film that supports a self-assembled monolayer formed from decanethiol and hexadecanethiol that causes nematic phases of 5CB to orient perpendicular to the mixed monolayer. A thin film of Mylar (thickness 10-20 micrometers) is used to separate the two surfaces and secured using a bulldog clip. 5CB is heated into its isotropic phase and introduced into the cavity between the two surfaces by using capillary forces, and then the 5CB is allowed to cool to room temperature, thus forming a nematic phase. The liquid crystal cell is placed into a polarized light microscope and viewed between crossed-polars (in transmission). The area of the hydrophobic monolayer on which the droplet of BSA causes the liquid crystal to assume a non-uniform orientation whereas the region of the surface that does not possess BSA non-specifically adsorbed to the surface causes a uniform alignment of the liquid crystal. Thus, the liquid crystal is demonstrated to be useful for imaging of non-specific adsorption of BSA to the surface.

Example 2

This Example describes the detection of non-specific adsorption of a molecule to a surface. In particular, this example describes detection of the non-specific binding of the BSA to the SAM formed from hexadecanethiol. An electron beam evaporator is used to obliquely deposit 30 Angstroms of titanium and then 130 Angstroms of gold onto immobile glass microscope slides. The rate of deposition of the metals is 0.2 Angstroms/sec and the angle of deposition is 50 degrees from the normal. This gold film is immersed into an ethanolic solution of hexadecanethiol to form a hydrophobic monolayer on the surface of the gold film. Next, BSA is adsorbed to the gold film at a level that does not cause liquid crystal on the surface to assume a non-uniform orientation. Anti-BSA IgG in Triton X-100 (to prevent non-specific adsorption of the IgG) is then bound to the BSA. The bound anti-biotin IgG is imaged by placing liquid crystal on the surface.

Example 3

This Example describes the detection of non-specific adsorption of a molecule to a surface. First, a cellulose nitrate film is mechanically rubbed so that it uniformly aligns liquid crystal. Proteins separated by gel electrophoresis are transferred onto the surface of the rubbed film by standard Western blotting procedures. The bands of transferred proteins are imaged by placement of liquid crystal on the rubbed film.

Example 4

This Example describes the detection of non-specific adsorption of a molecule to a surface. An electron beam evaporator is used to obliquely deposit 30 Angstroms of titanium and then 130 Angstroms of gold onto immobile glass microscope slides. The rate of deposition of the metals is 0.2 Angstroms/sec and the angle of deposition is 50 degrees from the normal. Monolayers formed from $HS(CH_2)_8N^+(CH_3)_3$ and $HS(CH_2)_2SO_3^-$ are then patterned on the surface to form regions that present $SO_3^-$ or $N^+(CH_3)_3$ groups. A microfluidic channel molded in PDMS is then placed on the patterned surface. Two proteins are flowed across the patterned surface at a pH such that one protein is above its pI whereas the other protein is below it. Thus one protein will adsorb onto the negatively charged region of the surface whereas the other protein will adsorb onto the positively charged region. An example of a protein pair is cytochrome-C (pI=10.7) and beta-lactoglobulin (pI=5.2), and use of PBS at 6.9. The surface is rinsed with PBS and then with water. Binding is imaged with a liquid crystal by forming a liquid crystal cell.

Example 5

This Example describes the detection of non-specific adsorption of a molecule to a surface. An electron beam evaporator is used to obliquely deposit 30 Angstroms of titanium and then 130 Angstroms of gold onto immobile glass microscope slides. The rate of deposition of the metals is 0.2 Angstroms/sec and the angle of deposition is 50 degrees from the normal. A region of biotin-terminated monolayers is patterned on the surface of the gold. The remainder of the surface is filled in using hexadecanethiol (so as to create a hydrophobic surface). Next, using a microfluidic channel molded in PDMS, anti-biotin IgG in PBS is flowed across the biotin region then hydrophobic region of the surface. The microfluidic channel is designed such that all anti-biotin IgG in the channel is captured by the biotin-terminated region of the surface. The surface is imaged by using liquid crystals in a liquid crystal cell. Inspection of the hydrophobic region of the surface will reveal if there are proteins in the sample other than the antibody (i.e., impurities). Thus this assay is useful for quality control. This experiment is repeated with BSA doped into the anti-biotin IG. The presence of the BSA is detected by non-uniform orientation of the liquid crystal on the hydrophobic region of the surface.

Example 6

This Example describes the preparation of an anisotropic surface by nanoblasting. First, glass microscope slides are cleaned using pirana solution ($H_2O_2/H_2SO_4$). Caution must be used because this solution has been reported to detonate upon contact with organic materials. Beads (50-1000 nm) are sprayed onto the surface of the glass microscope slides using a commercial abrasive spraying device (nanoblaster). A fixed direction of incidence is used with an angle of incidence of 45 degrees, measured from the normal of the substrate. The surface of the glass slides is then functionalized by using aminopropyltrimethoxysilane. The functionalized glass surface is activated by immersion into DSS. The activated glass microscope slide is immersed into an aqueous solution of BSA. The surface is rinsed with PBS and then with water. Next, two microscope slides prepared as just described are assembled into an optical cell. The slides are spaced apart by using a 20 micrometer-thick film of Mylar. The two slides are clipped together using bulldog clips. 5CB is heated into its isotropic phase and wicked between the two surfaces that define the optical cavity of the cell. The sample is allowed to cool to room temperature and then the optical cell is observed in transmission using a polarized light microscope. When viewed between crossed polarizers, the sample will appear bright and dark (sequentially) when rotated.

Example 7

This Example describes the preparation of an anisotropic surface by nanoblasting. First, glass microscope slides are cleaned using pirana solution ($H_2O_2/H_2SO_4$). Caution must be used because this solution has been reported to detonate upon contact with organic materials. Beads (50-100 nm) are sprayed onto the surface of the glass microscope slides using a commercial nanoblaster. A fixed direction of incidence is used with an angle of incidence of 45 degrees, measured from the normal of the substrate. The surface of the glass slides is then functionalized by using aminopropyltrimethoxysilane. The functionalized glass surface is activated by immersion into DSS. The activated glass microscope slide is immersed into an aqueous solution of biotinylated BSA. The surface is rinsed with PBS and then with water. The glass microscope slide presenting biotinylated BSA is then immersed into an aqueous solution containing 1 micromolar of 100 nm-sized, streptavidin-coated beads. The surface is rinsed with PBS and then with water. Next, two microscope slides prepared as just described are assembled into an optical cell. The slides are spaced apart by using a 20 micrometer-thick film of Mylar. The two slides are clipped together using bulldog clips. 5CB is heated into its isotropic phase and wicked between the two surfaces that define the optical cavity of the cell. The sample is allowed to cool to room temperature and then the optical cell is observed in transmission using a polarized light microscope. When viewed between crossed polarizers, the sample appears non-uniform because the beads bound to the surface will have erased the anisotropy introduced by the process of nanoblasting.

Example 8

This Example describes the preparation of an anisotropic surface by nanoblasting. First, glass microscope slides are cleaned using pirhana solution ($H_2O_2/H_2SO_4$). Caution must be used because this solution has been reported to detonate upon contact with organic materials. Beads (50-100 nm) are sprayed onto the surface of the glass microscope slides using a commercial nanoblaster. A fixed direction of incidence is used with an angle of incidence of 45 degrees, measured from the normal of the substrate. Next, a gold film is obliquely deposited on the surface of the nanoblasted microscope slide at an angle of deposition of 50 degrees (measured from the normal). An electron beam evaporator is used to obliquely deposit 30 Angtroms of titanium and then 130 Angstroms of gold onto immobile glass microscope slides. The rate of deposition of the metals is 0.2 Angstroms/sec. The film is deposited with an azimthual direction of incidence that is parallel to that used to nanoblast the surface. Biotinylated BSA is then adsorbed onto the surface of the gold. The protein-coated substrate is then immersed into an aqueous solution containing 1 micromolar concentration of avidin-coated, 100 nm diameter beads. Two microscope slides prepared as just described are then assembled into an optical cell. The two surfaces are spaced apart by using a 20 micrometer-thick film of Mylar and clipped together using bulldog clips. Next, 5CB is heated into its isotropic phase and wicked between the two surfaces that define the optical cavity of the cell. The sample is allowed to cool to room temperature and then observe the optical cell in transmission using a polarized light microscope. When viewed between crossed polarizers, the sample appears non-uniform.

Example 9

This Example describes the preparation of an anisotropic surface by stretching a substrate. First, a sheet of polystyrene is heated above its glass transition temperature. A tensile stress is then applied by pulling at its two ends, and then the substrate is cooled below the glass transition temperature prior to releasing the tensile stress. An optical cell is then fabricated from the stretched polymer film and an OTS-coated glass microscope slide. OTS-coated glass microscope slides are known to cause perpendicular (homeotropic alignment) of liquid crystals. The two surfaces are spaced apart using 20 micrometer-thick film of Mylar. The cell is then mounted in a polarized light microscope with an optical compensator. The compensator is adjusted to compensate for any stress-induced birefringence in the polystyrene. Next, 5CB is heated into its isotropic phase and draw it into the optical cell by using capillary action. The optical appearance of the 5CB is observed without further adjustment of the compensator. The 5CB appears uniformly dark or bright between crossed-polarized, indicating uniform alignment of the liquid crystal on the stretched polymer surface.

Example 10

This Example describes the fabrication of heterogenous surfaces for use in LC assays. A one-millimeter-thick slab of PDMS is cast on the surface of a planar substrate. The PDMS is peeled from the surface of the planar substrate and wrapped around the surface of a cylinder with a diameter of 3 centimeters. The PDMS is held onto the cylinder by using rubber bands. Gold film is evaporated onto the surface of the PDMS wrapped around the cylinder. An electron beam evaporator is used to obliquely deposit 30 Angtroms of titanium and then 130 Angstroms of gold onto the PDMS. The rate of deposition of the metals is 0.2 Angstroms/sec. The gold coated PDMS is released from the cylinder and mounted on the surface of a glass microscope slide. A self-assembled monolayer of hexadecanethiol is formed on the surface of the gold film by placing a droplet of a 1 mM ethanolic solution of PDMS onto the surface of the gold for 1 minute. The surface is rinsed with ethanol and then dried under a stream of nitrogen. The gold coated PDMS is then assembled into an optical cell using a second surface formed from OTS-coated glass microscope slide. The two surfaces forming the optical cell are spaced apart by 20 micrometers by using Mylar spacing material. 5CB is heated into its isotropic phase and wicked between the two surfaces by capillary action. The optical appearance of the 5CB, once cooled to room temperature, is examined with a polarized light microscope using crossed polars. The region of the surface onto which the gold is deposited at normal or near-normal incidence causes non-uniform anchoring of the liquid crystal. That is, the liquid crystal in this region of the surface is non-uniformly oriented. Away from this region, where the gold is deposited with an angle of incidence larger than 10 degrees, the anisotropy in the gold film causes the liquid crystal to assume a uniform orientation. Thus, there is a gradient in the appearance of the liquid crystal (from non-uniform to uniform).

Example 11

This Example describes the fabrication of heterogenous surfaces for use in LC assays. A glass microscope slide is heated in a bunsen burner. When the glass is soft, the microscope slide is bent such that the two planar ends of it define an angle of 150 degrees (i.e., it is bent by 30 degrees). The microscope slide looks like a "V". The glass microscope slide is cleaned in pirhana solution. The glass microscope slide is then mounted in an electron beam evaporator, such that one surface of the microscope slide is oriented at 30 degrees from the incident flux of gold; and the second region of the microscope slide is oriented at an angle of 60 degrees from the incidence flux of gold.

The electron beam evaporator is used to obliquely deposit 30 Angtroms of titanium and then 130 Angstroms of gold onto the PDMS. The rate of deposition of the metals is 0.2 Angstroms/sec. A self-assembled monolayer is then formed from hexadecane thiol on the surface of the gold film by immersion into a 1 mM ethanolic solution of hexadecanethiol. Next, BSA is adsorbed onto the hydrophobic SAM supported on the surface of the gold film. Two pieces of OTS-coated glass are then mounted on the gold film using 10 micrometer-thick Mylar spacers. The two cavities of the optical cell are filled with 5CB heated into its isotropic phase. The 5CB is then allowed to cool within the cavity. The appearance of the liquid crystal is observed using a polarized light microscope. On the region of the optical cell with gold film deposited at an angle of incidence of 30 degrees, the appearance of the liquid crystal is non-uniform. In contrast, in the region of the optical cell with the gold film deposited at an angle of incidence of 60 degrees, the liquid crystal appears uniform.

Example 12

This Example describes the fabrication of heterogenous surfaces for use in LC assays. Gold is obliquely deposited onto glass diffraction grating (blaze angle of 15 degree and a very long period) at a nominal angle of incidence of 45 degrees from the normal of the grating. Due to the blaze angle, one surface of the grating will be coated with gold that deposits at 30 degrees whereas the other surface will be coated with gold incident at an angle of 60 degrees. A mixed monolayer is formed on the surface of the gold film that presents biotin. Various samples are prepared that bind different amounts of anti-biotin IgG. Optical microscopy is then used to record the optical appearance of the liquid crystal as a function of the amount of bound anti-biotin IgG. The optical response of the liquid crystal on the grating surface is compared to the optical response on a surface that is planar. On the grating surface, the dynamic range of the response of the liquid crystal is larger.

Example 13

This Example describes LC assays prepared with a dichroic dye. A rubbed film of chemically immobilized biotinylated BSA is prepared. Next, a dichroic dye (0.01%), such as azobenzene, is mixed into 5CB. The dye/5CB mixture is then heated into its isotropic phase. The rubbed film is used to form an LC assay cell. The LC assay in then placed into a UV-Vis spectrophotometer without a polarizer and a scan between 180 nm and 800 nm is run for different orientations of the sample in the spectrophotometer. These steps are then repeated, except that anti-biotin IgG is bound onto the surface of the rubbed film. Additionally, a parallel experiment is performed wherein a polarizing filter is placed before the sample so that the sample is illuminated with polarized incident light. Whereas the absorbance spectrum of the cell prior to the binding of IgG is highly dependent on the orientation of the cell within the spectrophotometer, relatively little modulation in the intensity is seen when IgG is bound to the surface of the rubbed film of biotinylated BSA.

Example 14

This Example describes LC assays prepared with a fluorescent agent. A rubbed film of chemically immobilized biotinylated BSA is prepared. Next, an anisometric fluorescent dye (0.01%), such as BTBP, is mixed into 5CB. The dye/5CB mixture is then heated into its isotropic phase. The rubbed film is used to form an LC assay cell. The LC assay in then placed into a fluorimeter (excitation at 488 nm) and the fluorescence at 510-550 nm determined. These steps are then repeated, except that anti-biotin IgG is bound onto the surface of the rubbed film. Additionally, a parallel experiment is performed wherein a polarizing filter is placed before the sample so that the sample is illuminated with polarized incident light. Whereas the fluorescence from the cell prior to the binding of IgG is highly dependent on the orientation of the cell within the fluorimeter, relatively little modulation in the intensity is seen when IgG is bound to the surface of the rubbed film of biotinylated BSA.

Example 15

This Example describes the detection and quantification of bound analyte by measurement of the threshold electrical field required to change the orientation of the liquid crystal. First, a gold film is obliquely deposited onto a glass microscope slide as described in detail above. A mixed, biotin presenting monolayer is then prepared on the gold film (as described above). The slide is then half-dipped into an aqueous solution containing anti-biotin IgG. An optical cell is then assembled from two surfaces—one surface is the half-dipped sample and the second surface is a SAM formed from hexadecanethiol on gold. One end of the film is spaced apart using a ~1 micrometer-thick spacer and space the other end of the cell with a 50 micrometer thick spacer. The cell is then filled with 5CB. An AC electric field is then applied and, using a polarized light microscope, the propagation of the reoriented liquid crystal across the wedge (the LC will reorient first at the thin end of the cell) is determined as a function of the magnitude of the applied voltage.

Example 16

This Example describes the detection and quantification of bound analyte by measurement of the threshold electrical field required to change the orientation of the liquid crystal. First, a gold film is obliquely deposited onto a glass microscope slide as described in detail above. A mixed, biotin presenting monolayer is then prepared on the gold film (as described above). The slide is then dipped into an aqueous solution containing anto-biotin IgG. An optical cell is then assembled from two surfaces—one surface is the half-dipped sample and the second surface is a SAM formed from hexadecanethiol on gold. The two surfaces are spaced apart by using a ~5 micrometer-thick spacer. The cell is then filled with 5CB. An AC electric field is then applied and, using a polarized light microscope, the threshold voltage required to observe or measure a change in orientation of the liquid crystal is determined.

Example 17

This example describes the detection of non-specific adsorption of BSA to a surface. An electron beam evaporator was used to obliquely deposit approximately 30 Angstroms of titanium and subsequently approximately 300 Angstroms of gold onto an immobilized glass microscope slide. The rate of deposition of the metals was 0.2 Angstroms/sec and the angle of deposition was 69.5° from the normal. The gold substrate was then immersed into a 10 μM solution of bovine serum albumin (BSA) in PBS and incubated at room temperature for two hours. The BSA was then rinsed from the substrate using distilled, deionized water (ddH20) and dried under a stream of nitrogen. The BSA-adsorbed gold slide was then paired with an octadecyltrichlorosilane (OTS)-treated glass slide that caused the nematic phases of the 5CB liquid crystal to orient perpendicular to the BSA-adsorbed gold slide. A thin film of Mylar (thickness 20 μm) was used to separate the two surfaces, which was then secured using two small binder clips. Liquid crystal (5CB) was heated into its isotropic phase and introduced into the cavity between the two surfaces by capillary forces. The entire liquid crystal cell was placed into a polarized light microscope and viewed between cross-polars (in transmission). The BSA that adsorbed onto the gold surface caused the liquid crystal to assume a non-uniform orientation, as depicted in FIG. 3, whereas the surfaces that do not possess BSA non-specifically adsorbed to the surface caused uniform alignment of the liquid crystal (FIG. 4). Thus, the liquid crystal was shown to be useful for the imaging of non-specific adsorption of a molecule to a surface.

Example 18

Figure 6A:
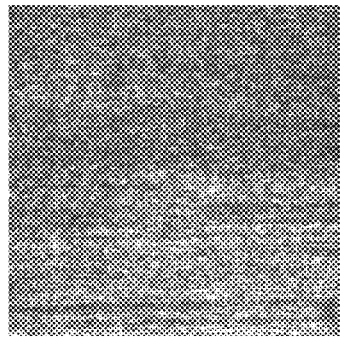
FIGS. 6A and 6B show optical textures of 5CB (crossed polarizers) sandwiched between stretched Parafilm and OTS-coated glass microscope slides. The optical textures shown in FIG. 6B were obtained after rotation of the cell shown in FIG. 5A by 45°.
Figure 6B:
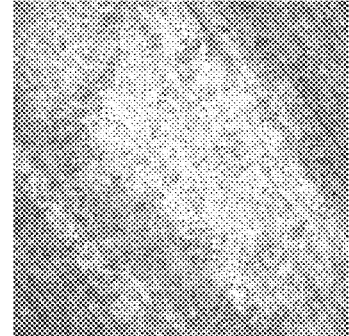

This example describes the preparation of an anisotropic surface by stretching a substrate. First, a small sheet of Parafilm was stretched by pulling at the two opposing edges. It was then mounted on top of a glass microscope slide using two-sided tape at one edge of the glass slide to hold the Parafilm securely in place. An optical cell was then fabricated from the stretched substrate and an OTS-coated glass microscope slide. OTS coated microscope slides are known to cause perpendicular (homeotropic alignment) of liquid crystals. The two surfaces were spaced apart using a 50 μm thick film of Mylar. Liquid crystal (5CB) is heated into its isotropic phase and placed on top of the substrate. The OTS slide was gently placed on top of the substrate, with care taken to avoid any air bubbles. Both non-stretched (FIG. 5)

and stretched Parafilm (FIG. 6) were analyzed. The 5CB liquid crystal appears uniformly dark or bright between crossed-polarizers, indicating uniform alignment of the liquid crystal on the stretched polymer surface. These results demonstrate that the Parafilm was already stretched in the manufacturing process, and thus additional stretching did not affect the homeotropic alignment when coupled with an OTS-coated slide.

Example 19

Figure 7A:
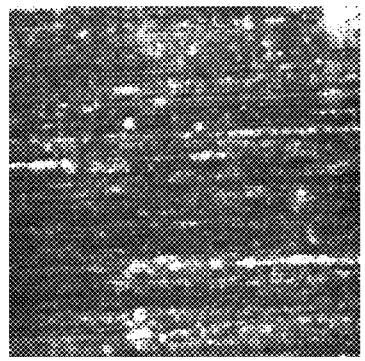
FIGS. 7A-7B show the effect of a rough microscope slide on optical appearance.
Figure 7B:
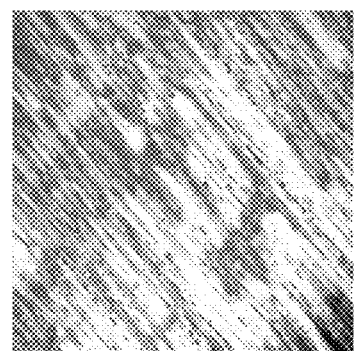

This Example describes a second experiment that further described the preparation of an anisotropic surface by stretching a substrate. A small strip of Parafilm was incubated in 10 mg/mL BSA in PBS at room temperature for two hours. The BSA was rinsed off of the glass microscope slide using ddH20 and dried under a stream of nitrogen. The liquid crystal cell was fabricated and loaded in same fashion as described above in Example 18. FIGS. 7 and 8 show that BSA was able to adsorb into both the stretched and non-stretched Parafilm, as indicated by the pronounced color modulation upon rotation (under crossed-polarizers) by 45°. Modulation was also observed in the stretched Parafilm indicating homeotropic alignment.

Example 20

This Example describes liquid crystal assays prepared with azobenzene, a dichroic dye. One cell was fabricated from two OTS-coated glass microscope slides, which produces homeotropic alignment of the liquid crystal, and a second cell was fabricated by pairing a rubbed BSA (0.1 mg/ml) glass microscope slide together with a regular glass microscope slide, which produces planar alignment of the liquid crystal. Next, the azobenzene dye was mixed into the 5CB liquid crystal. The dye/5CB mixture was then heated into its isotropic phase and injected into each of the cells via capillary action. The liquid crystal cell was then mounted into a UV-VIS spectrophotometer (Shimadzu Bio-Spec 1601, Shimadzu, Kyoto, Japan) and a scan between 190 nm and 800 nm was run for each of the different orientations. The results showed an absorbance peak at ~447 nm which was more intense for the planar orientation of the liquid crystal (0.362) than the homeotropic orientation (0.200). Thus, absorbance readings were able to distinguish between the various orientations of the liquid crystal.

Example 21

This Example describes an example similar to that described in Example 20 above. In this case, BTBP (N,N'-Bis(2,5-di-tert-butylphenyl)-3,4,9,10-perylenedicarboximide) was used. This example describes liquid crystal assays prepared with BTBP. One cell was fabricated to give homeotropic alignment of the liquid crystal and one cell to give planar liquid crystal alignment (see Example 20). Next, BTBP dye was mixed into the 5CB liquid crystal. The dye/5CB mixture was then heated into its isotropic phase and injected into each of the cells via capillary action. The liquid crystal cell was then mounted into a UV-VIS spectrophotometer (Shimadzu Bio-Spec 1601) and a scan between 190 nm and 800 nm was run for each of the different orientations. The results showed three absorbance peaks at ~532 nm, 495 nm, and 464 nm. As observed in Example 21, the absorbance values were more intense for the planar orientation (0.364, 0.308, 0.224 respectively) as compared to 0.250, 0.193, and 0.128 for the homeotropic orientation. Thus, initial absorbance readings were able to distinguish between the various orientations of the liquid crystal.

Example 22

This example describes the detection and quantification of a bound analyte by measurement of the threshold electrical field required to change the orientation of the liquid crystal. First, a gold film was obliquely deposited onto a glass microscope slide. An electron beam evaporator was used to obliquely deposit ~30 Angstroms of titanium and then ~300 Angstroms of gold onto an immobilized glass microscope slide. The rate of deposition of the metals was 0.2 Angstroms/sec and the angle of deposition was 30° from the normal. The slide was then half-dipped into an aqueous solution of 0.1 mg/ml BSA and allowed to incubate for at room temperature for two hours. The BSA was then rinsed from the glass slide with $ddH_2O$ and dried under a stream of nitrogen. An optical cell was then assembled from two surfaces—one surface was the half-dipped BSA glass microscope slide and the second surface was a regular obliquely-coated (30°) gold microscope slide. The two surfaces were spaced using ~4 μm Saran Wrap. The cell was then filled with liquid crystal (5CB). A DC electric field is applied and, using a polarized light microscope, the threshold voltage required to observe or measure a change in orientation of the liquid crystal was determined. A voltage of ~6.5 V was necessary to see the beginnings of an orientational liquid crystal change. The untreated gold portion of the glass microscope slide appeared to change first, whereas the BSA-treated half started to change shortly thereafter. Upon ramping the voltage to ~15 V, the entire sample showed homeotropic liquid crystal alignment (as indicated by a "black-cross" when viewed with a Bertrand microscope lens.) Thus, the application of an electrical field allows for the detection of a bound protein by altering the orientation of liquid crystal.

Example 23

This example describes the preparation of an anisotropic surface by texturizing a substrate (nanoblasting). First, glass microscope slides were cleaned using an LF-5 Plasma Asher (Mercator Control Systems, Inc). The glass microscope slides were then texturized by rubbing a fine 320-grit sandpaper pad (3M, St. Paul, Minn.) across the surface of the slide in a uniform direction approximately five times (keeping the pressure fairly constant). The rubbing distance was approximately thirteen centimeters. An optical cell was then fabricated from the textured glass slide and a clean glass microscope slide, with a 20 μm Mylar spacer placed in between. Liquid crystal (5CB) was heated into its isotropic phase and injected between the two surfaces via capillary action. The cell was allowed to cool and then observed under a polarizing microscope.

The results are shown in FIG. 7. When viewed between cross polarizers, the cell appears bright and dark (sequentially) when rotated. Thus, the anisostropic surface prepared by roughening the substrate resulted in a uniform alignment of the liquid crystal.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in organic chemistry, materials science, chemical engineering, virology, biology, genetics, or related fields are intended to be within the scope of the following claims.

What is claimed is:

1. A system for detecting an analyte in a sample comprising:
   a. at least one substrate having a surface comprising recognition moieties;
   b. a mesogenic layer oriented on said surface;
   c. electrodes positioned to apply an electrical field across said surface comprising recognition moieties.

2. The system of claim 1, wherein said system further comprises an interface between said mesogenic layer and a member selected from the group consisting of gases, liquids, solids, and combinations thereof.

3. The system of claim 1, wherein said recognition moiety is attached to said surface by an interaction which is a member selected from the group consisting of covalent bonding, ionic bonding, chemisorption, physisorption, and combinations thereof.

4. The system of claim 1, wherein said surface further comprises an organic layer.

5. The system of claim 4, wherein said recognition moiety is attached to said organic layer by an interaction which is a member selected from the group consisting of covalent bonding, ionic bonding, chemisorption, physisorption, and combinations thereof.

6. The system of claim 1, wherein said mesogenic layer comprises a polymeric mesogen.

7. The system of claim 1, wherein said mesogenic layer comprises mesogens selected from the group consisting of 4 cyano 4' pentylbiphenyl, N (4-methoxybenzylidene) 4 butylaniline and combinations thereof.

8. The system of claim 1, wherein said mesogenic layer comprises a lyotropic liquid crystal.

9. The system of claim 1, wherein said surface is a metal surface.

10. The system of claim 9, wherein said metal surface is selected from the group consisting of gold, platinum, palladium, copper, nickel, silver, and combinations thereof.

11. The system of claim 1, wherein said substrate is selected from the group consisting of flexible substrates, rigid substrates, optically opaque substrates, optically transparent substrates, conducting substrates, semiconducting substrates, and combinations thereof.

12. The system of claim 1, wherein said substrate is selected from the group consisting of inorganic crystals, inorganic glasses, inorganic oxides, metals, organic polymers, and combinations thereof.

13. The system of claim 12, wherein said organic polymer is selected from the group consisting of polyvinylidene fluoride, polydimethylsiloxane, polycarbonate, polystyrene, polyurethane, polyisocyanoacrylate, epoxy and combinations thereof.

14. The system of claim 1, wherein said analyte is selected from the group consisting of polypeptides, polynucleotides, organic analytes, and pathogens.

15. The system of claim 1, wherein said recognition moiety is selected from the group consisting of polynucleotides, antigen binding molecules, and polypeptides.

* * * * *